US010399713B2

(12) United States Patent
Py et al.

(10) Patent No.: US 10,399,713 B2
(45) Date of Patent: Sep. 3, 2019

(54) DEVICES AND METHODS FOR FORMULATION PROCESSING

(71) Applicant: Dr. Py Institute LLC, New Milford, CT (US)

(72) Inventors: Daniel Py, Larchmont, NY (US);
Debashis Sahoo, Danbury, CT (US);
Julian V. Chan, New Milford, CT (US)

(73) Assignee: DR. PY INSTITUTE LLC, New Milford, CT (US)

( * ) Notice: Subject to any disclaimer, the term of this patent is extended or adjusted under 35 U.S.C. 154(b) by 283 days.

(21) Appl. No.: 15/410,758

(22) Filed: Jan. 19, 2017

(65) Prior Publication Data

US 2017/0203860 A1    Jul. 20, 2017

Related U.S. Application Data

(60) Provisional application No. 62/280,696, filed on Jan. 19, 2016.

(51) Int. Cl.
*B65B 3/00* (2006.01)
*A61J 1/20* (2006.01)
(Continued)

(52) U.S. Cl.
CPC ............ *B65B 3/003* (2013.01); *A61J 1/2048* (2015.05); *A61M 39/10* (2013.01); *B65B 3/12* (2013.01);
(Continued)

(58) Field of Classification Search
CPC ..... B65B 3/00; B65B 3/34; B65B 3/36; A61J 1/2048; A61M 39/10
(Continued)

(56) References Cited

U.S. PATENT DOCUMENTS 7,392,698 B2 * 7/2008 Zalite .................. G01F 25/0007
73/220
8,181,911 B1 * 5/2012 Gryniewski ............. B25J 11/00
244/172.5
(Continued)

FOREIGN PATENT DOCUMENTS

| DE | 102006049347 A1 | 4/2008 |
| EP | 0923350 B1 | 7/2003 |
| WO | 2015195842 A1 | 12/2015 |

OTHER PUBLICATIONS

International Search Report and Written Opinion issued in International Application No. PCT/US2017/014201 dated May 26, 2017. 19 pages.

*Primary Examiner* — Timothy L Maust
(74) *Attorney, Agent, or Firm* — McCarter & English, LLP

(57) ABSTRACT

Apparatuses and methods for controlling transfer of substances to a formulation container to provide a predetermined formulation. A controller may utilize one or more of a flow time, flow rate or a volume of transfer of substance. Barcoded and RFID-containing components may be used to determine what connection or disconnection has been made, and/or time thereof. Process compliance may compare measured or determined flow or connection time, flow rate and/or the transfer volume to a predetermined time, flow rate and/or volume, and adjust one or more of the time, flow rate and/or the volume of the transfer. An optional holder or cradle is configured to receive therein a fluid transfer connector formed by the connection of first and second connector portions, each in fluid communication with a flow conduit or channel that delivers substance to or receives substance from its respective connector portion, only if the connector portions are properly connected together. One or more sensors may be used to determine identification information of the connector and/or flow rates of substance through the connector.

55 Claims, 11 Drawing Sheets

(51) Int. Cl.
    *B65B 3/12*     (2006.01)
    *B65B 3/28*     (2006.01)
    *B65B 3/30*     (2006.01)
    *B65B 3/36*     (2006.01)
    *A61M 39/10*     (2006.01)
    *A61J 3/00*     (2006.01)
    *B65B 55/08*     (2006.01)

(52) U.S. Cl.
    CPC ............... *B65B 3/28* (2013.01); *B65B 3/30* (2013.01); *B65B 3/36* (2013.01); *A61J 3/002* (2013.01); *A61J 2205/10* (2013.01); *A61J 2205/60* (2013.01); *B65B 55/08* (2013.01)

(58) Field of Classification Search
    USPC ......................................................... 141/94
    See application file for complete search history.

(56) References Cited

U.S. PATENT DOCUMENTS

| | | |
|---|---|---|
| 8,646,243 B2 | 2/2014 | Py |
| 9,134,736 B2* | 9/2015 | Lowery ............... G05D 7/0635 |
| 9,883,987 B2* | 2/2018 | Lopez ............... A61M 5/14228 |
| 2002/0170731 A1* | 11/2002 | Garber .................. B67D 7/348 174/47 |
| 2007/0169546 A1 | 7/2007 | Zalite et al. |
| 2008/0214990 A1* | 9/2008 | Smutney ............. A61M 3/0279 604/27 |
| 2009/0098250 A1 | 4/2009 | Py |
| 2012/0112009 A1 | 5/2012 | Gryniewski et al. |
| 2013/0083191 A1* | 4/2013 | Lowery ............... G05D 7/0635 348/135 |
| 2013/0270820 A1 | 10/2013 | Py |
| 2014/0290796 A1* | 10/2014 | Tribble .................. B65B 3/003 141/94 |
| 2014/0299221 A1* | 10/2014 | Lopez ............... A61M 5/14228 141/1 |
| 2015/0122369 A1 | 5/2015 | Py |
| 2015/0274329 A1* | 10/2015 | Harp ...................... A61J 1/20 53/474 |
| 2016/0129585 A1* | 5/2016 | Davis ................... G07F 11/165 141/165 |
| 2016/0178101 A1* | 6/2016 | Blake ................ A61M 39/1011 285/417 |

* cited by examiner

DEVICES AND METHODS FOR FORMULATION PROCESSING

CROSS REFERENCE TO RELATED APPLICATIONS

This patent application claims benefit under 35 U.S.C. § 119 to U.S. provisional application No. 62/280,696, entitled "Formulation Processing," filed Jan. 19, 2016, which is expressly incorporated by reference as part of the present disclosure.

FIELD OF THE INVENTION

The present invention relates to apparatuses and methods for controlling and documenting transfer of substances for the manufacture of a formulation, and more particularly, to devices for use in controlling and documenting same, and to related methods of making and using same.

BACKGROUND INFORMATION

Generally, process control for the manufacturing or formulation of a product is important if not critical to providing a product of desired quality and/or that meets specifications. Deviation from the specified process can negatively affect quality, and in some situations can be dangerous. For some industries or products, deviation from specification may violate laws or regulations.

One industry in which specified product quality is often necessary is pharmaceutical manufacturing. Three main objectives typically govern the pharmaceutical manufacturing process. The first objective may be to maintain sterility of critical surfaces within the receiving chambers that contain the ingredient substances used in the manufacture and the manufactured formulations themselves. The second objective may be to maintain consistency and quality of the formulation being manufactured. Most formulations are a combination of different ingredients. These ingredients need to be blended in the most sustainable manner in order to ensure consistent quality of the resultant formulation for use by a patient. The third objective may be to avoid or limit particulate issues contaminating the ingredients as well as the formulation being manufactured. Traditional aseptic manufacturing involve a process by which sterile substances are transferred into sterile receiving chambers and the receiving chambers are closed after completion of filling—all within a classified environment.

SUMMARY OF THE INVENTION

Accordingly, it is an object of the present invention to overcome one or more of the above described drawbacks and/or disadvantages of the prior art.

In one aspect, apparatuses can be used to control transfer of a substance to maintain a predetermined formulation. The apparatus includes a cradle or holder having a body defining a first interior cavity portion therein configured to receive therein a fluid transfer connector formed by the connection of a first connector portion and a second connector portion. The cradle is configured and dimensioned to receive the connector therein only when the first connector and the second connector are properly connected together. In some embodiments, the first interior cavity portion includes a sensor configured to determine identification information of the connector, the apparatus may transmit such identification information to a controller configured to control fluid transfer flow though the connector. In some such embodiments, the connector includes an RFID tag, and the cradle includes an RFID reader. In other such embodiments, the connector contains a barcode, and the cradle includes a bar code reader.

In further embodiments, the cradle includes a detector configured to detect whether the connector is properly located within the first interior cavity portion, and transmits to the controller that the connector is and/or is not properly located within the first interior cavity portion. The detector may be mechanical, electromechanical, or electronic. In one embodiment, the detector includes a switch movable between a first position when the connector is not properly located in the first interior cavity portion and a second position when the connector is properly located in the first interior cavity portion. In the second position, information representing that the connector is properly located within the first interior cavity portion is transmitted to the controller. In a further embodiment, the switch is biased in a direction from the second position to the first position so as to provide a default a condition that the connector is not properly in the cavity.

In other embodiments, the cradle has a second interior cavity portion that receives a portion of a flow conduit in fluid communication with the connector. A flow meter measures flow of fluid through the flow conduit and transmits the measured flow to the controller.

The cradle may include a cover movable between open and closed positions. When opened, the connector and/or the flow conduit portion may be inserted into the cradle. When closed, access to the interior cavities of the cradle is blocked. In some such embodiments, the cradle includes a cover position detector configured that detects whether the cover is open or closed. When closed, the detector transmits information representing such to the controller. The detector can be mechanical, electromechanical, or electronic. In one embodiment, the detector includes a switch movable between a first position when the cover is open and a second position when the cover is closed. In the second position, information that the cover is closed is transmitted to the controller. In a further embodiment, the switch is biased in a direction from the second position to the first position so as to provide a default a condition that the cover is open.

In another aspect, methods are provided for controlling transfer of a substance to maintain a predetermined formulation. A first connector portion and a second connector portion of a fluid transfer connector are connected. The connector is into a cradle having a body with a first interior cavity portion configured and dimensioned to allow the connector therein only if when the first connector and the second connector are properly connected together, such that the connector is received in the first interior cavity portion. In some embodiments, the method includes sensing identification information of the connector, and transmitting said identification information to a controller configured to control fluid transfer flow though the connector. In some such embodiments, the connector includes an RFID tag, and an RFID reader senses the identification information. In other embodiments, the connector contains a barcode, and a bar code reader reads the identification information in the barcode.

In further embodiments, the method further includes detecting whether the connector is properly located within the first interior cavity portion, and if so, transmitting to the controller information representing such. In some such embodiments, the detecting includes moving a switch from a first position where the connector is not properly located in the first interior cavity portion to a second position where the connector is properly located in the first interior cavity portion, and performing the transmitting when the switch is in the second position. In further embodiments, the switch is biased in a direction from the second position to the first position to create a default condition that the connector is not properly located in the cavity.

In embodiments where the cradle includes a second interior cavity portion, a flow conduit in fluid communication with the connector is inserted into the second interior cavity portion and a flow meter measures flow in the conduit and transmits measurement information the controller.

In embodiments where the cradle includes a cover, the method may include detecting whether the cover is in an open position or a closed position, and if closed, transmitting such information to the controller. In some embodiments, such detection includes moving a switch from a first position where the cover is in the open position to a second position where the cover is in a closed position. In some such embodiments, the switch is biased in a direction from the second position to the first position to provide a default condition that cover is detected as being open.

A method as defined in claim 16, further including engaging a flow conduit in fluid communication with the connector with a pump configured to pump fluid in the flow conduit through the connector in the connected position.

One advantage of embodiments of the invention is that they determine and thus ensure that the connector is properly connected before substance is passed through the connector. Another advantage of embodiments of the invention is that they prevent uncontrolled human intervention and error in the production of a formulation. Another advantage of embodiments of the invention is that they enable high replication of product quality and composition among formulation lots, and also among different producers utilizing congruent formulation systems and process parameters.

Yet another advantage of embodiments of the invention is that they enable management of inventory and ingredients. A further advantage of embodiments of the invention is that they enable adjustment of the formulation process based on inventory to prevent deviation in formulation composition.

An additional advantage of embodiments of the invention is that they permit remote monitoring, inspection and auditing of the formulation process. Such remote activities may be performed using recorded information or live, real-time information.

Yet an additional advantage of embodiments of the invention is that they enable detection, mitigation and prevention of errors. For example, when two or more components or ingredients are to be mixed, mixing of incorrect ingredients can be avoided. The controller may be programmed to prevent the flow of ingredients, e.g., to a mixing device, unless the controller confirms, through information received by it that the correct connectors are installed into respective cradles. If the bar code or RFID read indicates that the connector installed in a cradle in the fluid path to the mixing apparatus is associated with a component that is not the component intended to be mixed, the controller may prevent the operation of the system. For example, the controller may stop operation of, or prevent or abstain from starting, a pump that would pump components to the mixing device. Likewise, the controller may close, or prevent or abstain from opening, valves controlling fluid flow from the component source to the mixing device. Further, in embodiment where the mixing apparatus is mechanical in nature, the controller may stop operation, of or prevent or abstain from operating, the mixing apparatus. These are merely exemplary, however. The controller may take any action, or not take any action, or combination of the same to prevent the flow and/or mixing of substances from taking place. In addition, the controller may activate an alarm or message informing a user of the error and the action(s) taken or not taken by the controller.

Other embodiments can ensure components are mixed in the correct sequence and/or prevent components from being mixed in the incorrect sequence. Some formulations are required to be combined a particular order. The controller may ensure that the components are mixed in the correct order by allowing flow of components to the mixing apparatus only in the correct order. The controller may also prevent flow of components to the mixing apparatus if doing so would cause the components to mix in the incorrect order. As an example, if a three-component formulation must be mixed in a certain order, the controller may be programmed with the proper sequence of ingredients, e.g., ingredients I and II need to be mixed before adding ingredient III. The controller can ensure that ingredient III is not connected to (placed in fluid communication with) the mixing chamber before ingredient II is connected and added to the mixing chamber (and in the correct amount per the formulation procedure). If a connector that is connected to an ingredient and assigned to that ingredient in system is not connected at the right time or sequence, e.g., as sensed by the cradle via the RFID for that connector, the system may be programmed to not allow that ingredient to flow to the mixing chamber, such as, but not limited to, controlling the operation of pertinent valves and/or pumps. Continuing with this example, if after ingredient I is added to mixing chamber the connector associated with ingredient III is connected to chamber, the system will read that such connector is currently connected (via RFID and the cradle), and, if so programmed, determine that it is the wrong connection, and issue an alarm and/or not allow the process to proceed—e.g., prevent pumps from operating or automatically shutting a valve in line by (a) preventing ingredient III from flowing out of its storage source (upstream of sterile connector) and/or (b) preventing ingredient III from flowing into mixing chamber (downstream of sterile connector but upstream of mixing chamber). Prevention step (a) prevents ingredient III from ever reaching the line that goes into the mixing chamber, where residual substance in the line can "contaminate" the formulation or be carried into the mixing chamber when the correct ingredient flows through the line.

Other embodiment may, alternatively or in addition, control or ensure proper residence time within a mixing or reaction chamber. For example, some formulations require that ingredients remain in the mixing and/or reaction chamber for a certain minimum period of time in order for a desired, specified or required amount of mixing to occur, e.g., sufficient mixing and/or homogenization, and/or for a sufficient reaction, e.g., chemical, mechanical, electrochemical, etc., to occur. Continuing with and modifying the above-discussed example, if ingredients I and II not only need to be mixed together prior to the addition of ingredient III, but also, reside in the mixing chamber for a certain period of time before adding ingredient III, e.g., to ensure full (or desired) mixing or diffusion of ingredients, the controller may be programmed with the desired, specified or necessary residence time (or range thereof). Via its connection with the system equipment (which may be wired, wireless, or a combination thereof), the controller can prevent or delay delivery of ingredient III to the mixing chamber (e.g., via control of valves, pumps, etc.) until the proper residence time is achieved. Conversely, if an ingredient, e.g., ingredient III is connected to the mixing chamber, as sensed by the cradle (bar code and/or RFID), and their has been an insufficient residence time, the control may prevent the process from proceeding and/or prevent ingredient III from flowing into the mixing chamber, e.g. prevent or shut down pumps from operating, automatically shutting a valve in the fluid path, etc. The system may also issue and alarm and/or notification of the status of the process. In other embodiments, a residence time may apply to a single ingredient rather than multiple ingredients, e.g., residence time for sufficient dissolution of an ingredient in a solvent, residence time for sufficient dilution of an ingredient to a desired, specified or required concentration, etc.

In other embodiments, the amount of ingredient or product delivered to a container, e.g., a mixing or storage container, by measuring the weight of the container. The container may be connected to or reside on a scale. The weight of the product delivered to the container may be determined, for example, by monitoring of a change in weight of the container during delivery of the product thereto. A current weight (or change thereof) read or measured by the scale may be transmitted to the controller. The controller may be programmed with the specified weight of the product or ingredient. The controller may then for example, help ensure the specified amount of product is added by 1) flowing substance to the container until the specified weight is added and/or 2) preventing or ceasing flow of substance in excess of specification, e.g., via control valves, pumps, etc. The system may also issue notifications or alarms to indicate process status, e.g., an overweight or underweight condition.

In further embodiments, process information and/or data as read or determined by the system may be recorded for current or future retrieval, monitoring, diagnosis, quality control or certification. Such activities may be conducted off-site via transmission or retrieval of such information and/or data.

Other objects and advantages of the present invention will become more readily apparent in view of the following detailed description of the currently preferred embodiments and the accompanying drawings. It should be understood by those of ordinary skill in the art that one or more features and/or embodiments of the invention, alone and/or in combination, may be utilized with respect to any parameter of a formulation or manufacturing process.

However, while various objects, features and/or advantages have been described in this Summary and/or will become more readily apparent in view of the following detailed description and accompanying drawings, it should be understood that such objects, features and/or advantages are not required in all aspects and embodiments.

This Summary is not exhaustive of the scope of the present aspects and embodiments. Thus, while certain aspects and embodiments have been presented and/or outlined in this Summary, it should be understood that the present aspects and embodiments are not limited to the aspects and embodiments in this Summary. Indeed, other aspects and embodiments, which may be similar to and/or different from, the aspects and embodiments presented in this Summary, will be apparent from the description, illustrations and/or claims, which follow.

It should also be understood that any aspects and embodiments that are described in this Summary and do not appear in the claims that follow are preserved for later presentation in this application or in one or more continuation patent applications.

It should also be understood that any aspects and embodiments that are not described in this Summary and do not appear in the claims that follow are also preserved for later presentation or in one or more continuation patent applications.

DETAILED DESCRIPTION OF EMBODIMENTS

Figure 1:
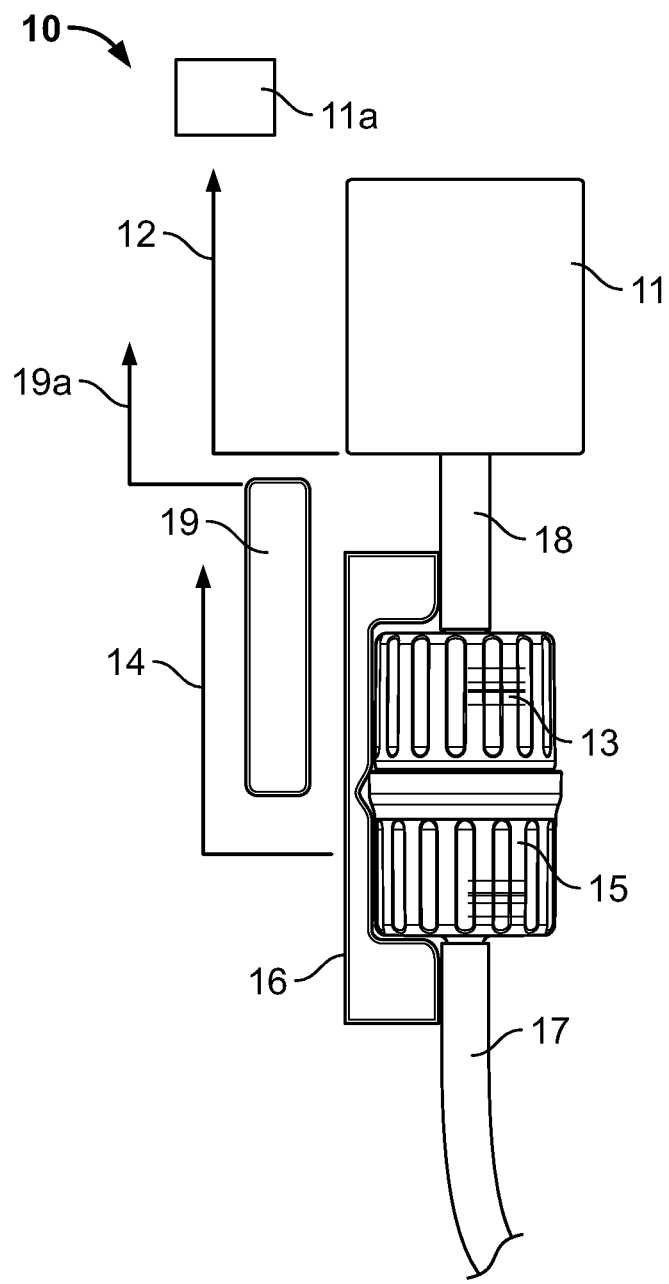
FIG. 1 is a schematic view of an apparatus configured to control transfer of a substance comprising, among other components, a flow meter and a connecting device, both in communication with a controller such as a process logic controller (PLC)

FIG. 1 shows an embodiment of an apparatus indicated generally by the reference numeral 10. The device 10 in combination with a controller 11a may be used to control transfer of substances to maintain a predetermined formulation of the resulting manufactured formulation. The apparatus described below can provide control of both small-scale and large-scale sterile filling, for example: for pharmaceutical and biotechnology research and development, university teaching, research, and development, clinical trials, analytical laboratories; at pharmacies, hospitals, doctor's offices, extended care facilities, and/or emergency and rescue operation areas for on-demand dispensing and production for customers and patients; at food processing plants; at facilities for manufacturing and formulation trials, research, and production; and can be used in emerging markets and countries.

Figure 2:
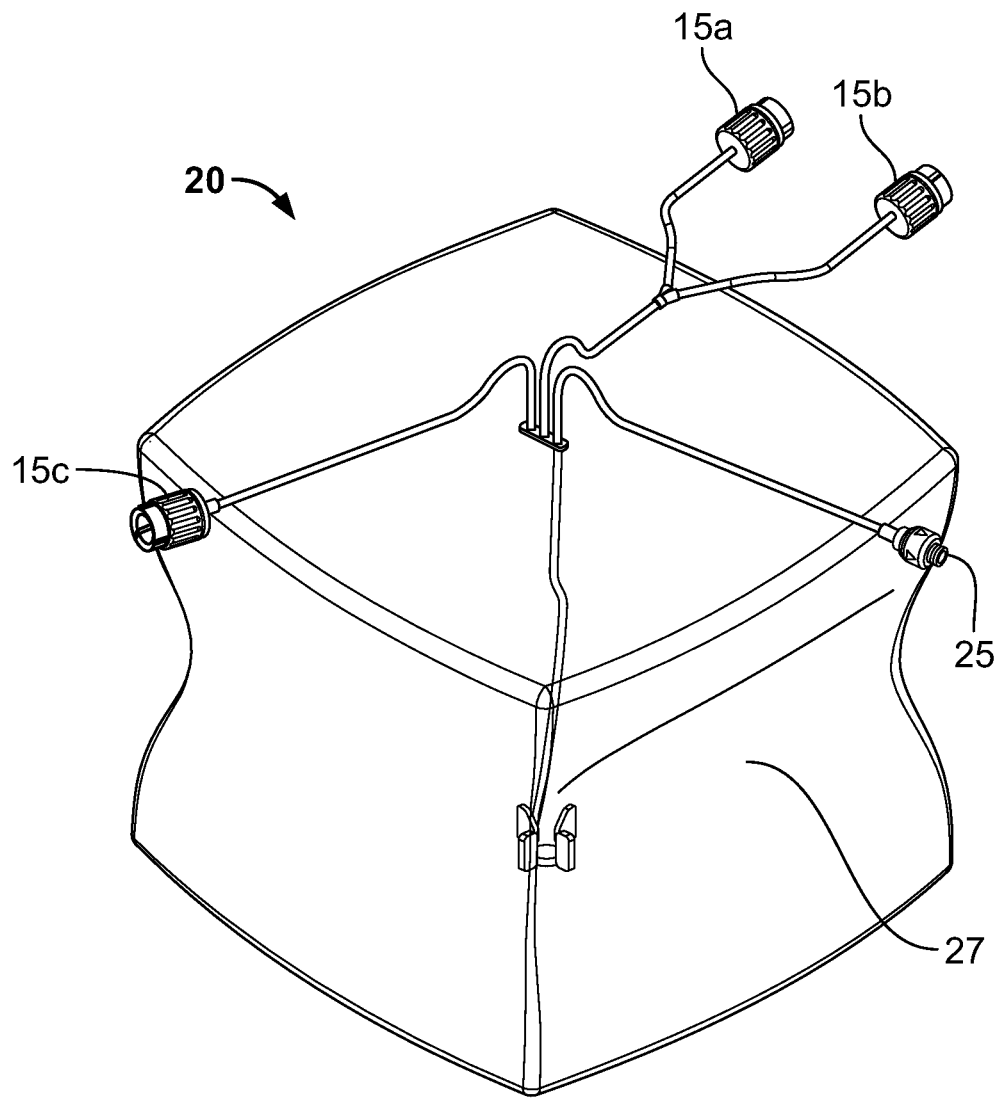
FIG. 2 is a perspective view of a formulation receiving chamber that receives transferred substances from one ore more of the apparatus of FIG. 1.
Figure 3:
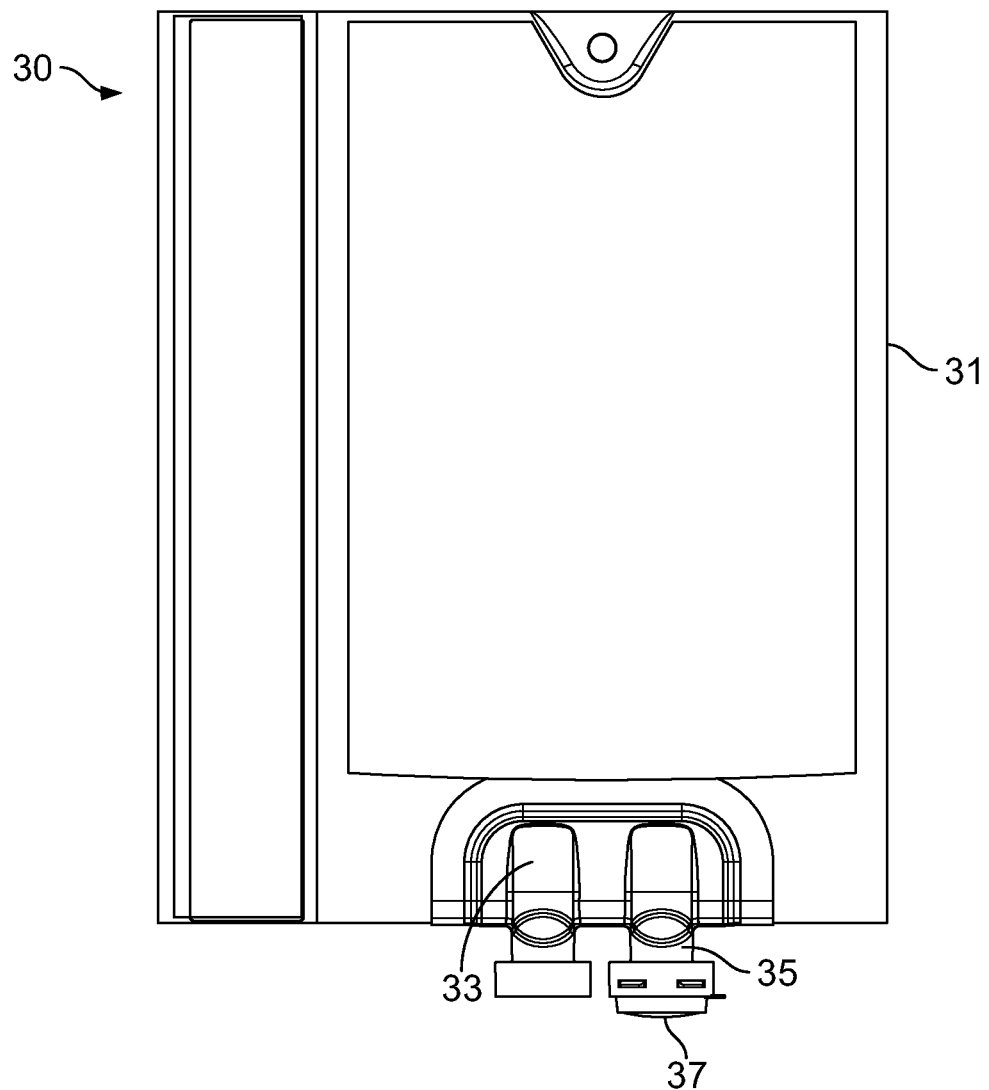
FIG. 3 is a front view of a pouch containing a substance to be transferred utilizing the apparatus of FIG. 1.

As shown in FIG. 1, the apparatus, in one embodiment, includes a flow meter 11, a barcoded first connector 13 in fluid connection with a substance contained in a substance source, such as but not limited to the pouch illustrated in FIG. 3, through a first conduit, tube or channel 18, a barcoded second connector 15 forming a fluid-tight hermetic connection with the first connector 13, a second conduit, tube or channel 17 in fluid communication with a formulation chamber, such as but not limited to the chamber illustrated in FIG. 2, a barcode reader 19, a connecting device 16, and communication channels 12, 14, and 19a that connect the flow meter 11, the connecting device 16, and the barcode reader 19 respectively to the controller 11a.

The barcoded first connector 13 and the barcoded second connector 15 may comprise connectors capable of forming a fluid-tight and/or hermetic seal. In some embodiments, the first connector 13 may comprise a sterile male connector and the second connector 15 may comprise a sterile female connector, or vice versa. Exemplary such sterile connectors are disclosed in the following patents and co-pending patent applications, each of which is hereby expressly incorporated by reference as part of the present disclosure: U.S. patent application Ser. No. 13/450,306, filed Apr. 18, 2012, entitled "Needle with Closure and Method," which claims the benefit of U.S. Provisional Application No. 61/476,523, filed Apr. 18, 2011, entitled "Filling Needle and Method"; U.S. patent application Ser. No. 13/861,502, filed Apr. 12, 2013, entitled "Modular Filling Apparatus and Method," now U.S. Pat. No. 8,966,866, which claims the benefit of similarly titled U.S. Provisional Application No. 61/686,867, filed Apr. 13, 2012; U.S. patent application Ser. No. 13/080,537, filed Apr. 5, 2011, entitled "Aseptic Connector with Deflectable Ring of Concern and Method", now U.S. Pat. No. 8,671,964, which claims the benefit of similarly titled U.S. Provisional Application No. 61/320,857, filed Apr. 5, 2010; U.S. patent application Ser. No. 13/864,919, filed Apr. 17, 2013, entitled "Self-Closing Connector", which claims the benefit of similarly titled U.S. Provisional Patent Application No. 61/635,258, filed Apr. 18, 2012, and similarly titled U.S. Provisional Patent Application No. 61/625,663, filed Apr. 17, 2012; U.S. patent application Ser. No. 13/874,839, filed May 1, 2013, entitled "Device for Connecting or Filling and Method", which claims the benefit of similarly titled U.S. Provisional Patent Application No. 61/641,248, filed May 1, 2012, and similarly titled U.S. Provisional Patent Application No. 61/794,255, filed Mar. 15, 2013; and U.S. patent application Ser. No. 14/536,566, filed Nov. 7, 2014, entitled "Device for Connecting or Filling and Method", which claims the benefit of similarly to similarly-titled U.S. Provisional Patent Application Nos. 61/641,248, filed May 1, 2012, and 61/794,255, filed Mar. 15, 2013, each of which is hereby expressly incorporated by reference in its entirety as part of the present disclosure as if fully set forth herein.

In one embodiment, one of the connectors is a female connector that is penetrable by a corresponding male connector to place the male and female connectors in sterile, fluid communication with each other, and to dispense the substance contained in pouch 30 (FIG. 3) into the formulation chamber 20 (FIG. 2) therefrom. In one embodiment, the first connector 13 is moved from a condition where it is not connected to the second connector 15 toward and into engagement with the second connector 15 by the connecting device 16 so that the first connector housing of the second connector 15 is slidably received within the connector housing of the first connector 13 to form a fluid-tight hermetic seal and a fluid path between the first connector 13 and the second connector 15.

As may be recognized by those of ordinary skill in the pertinent art based on the teachings herein, the fitments of the first and second connectors 13, 15 may take any of numerous different configurations that are currently known, or that later become known. For example, the fitment(s) may include only one septum, may include more than two septa, may include one or more septa and one or more sterile connectors, and/or may include one or more sterile connectors without any septa, and a pouch or other device may include more than one fitment. Further, the first and second connectors may include a closed needle and septum thereof.

The connecting device 16 may comprise any device now known or later developed that is capable of connecting and disconnecting the first and second connectors 13, 15. The connecting device 16, in one embodiment, is in communication with the controller 11a, and may be capable of connecting and disconnecting the first and second connectors based on signals received from the controller. The connecting device may also be coupled to the flow meter 11 with the flow meter being located either immediately upstream or immediately downstream (as in FIG. 1) of the connecting device 16.

In one embodiment, the flow meter 11 may comprise a device that measures, determines or meters the flow of a substance through the first channel 18. In one embodiment, the flow meter 11 may be capable of measuring the flow rate of the substance without making physical contact with the substance within the first conduit 18, e.g., located entirely externally thereto. The flow meter may use optical, laser, ultrasonic, magnetic or other technologies now known and later developed to measure the flow rate of the substance. The flow meter 11 may then communicate this information to the controller. In one embodiment, the controller comprises a process logic controller (PLC). The PLC controller may communicate with various components of the apparatus 10, and other components in the overall manufacturing environment either wirelessly or through wired connections, as should be understood by those of ordinary skill in the art.

Figure 4:
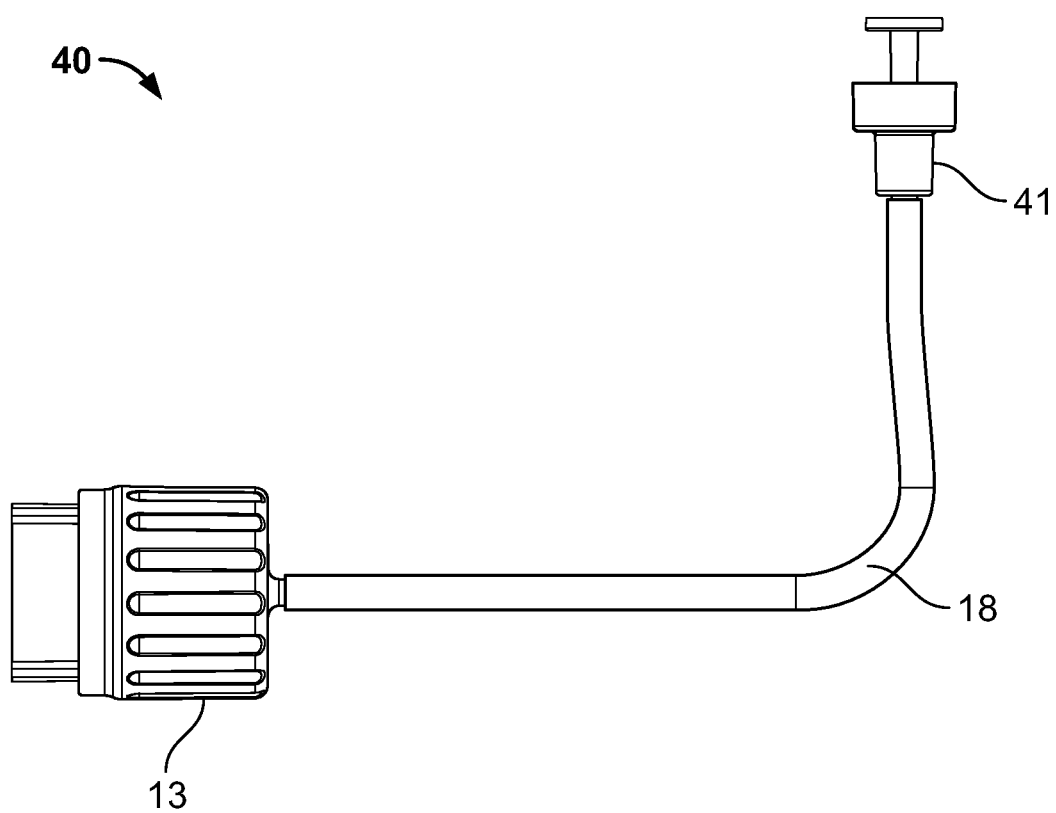
FIG. 4 is a side view of a connecting conduit with a single use connector on a first end and a first connector at a second end, the single use connector capable of forming a fluid-tight and/or hermetic connection with a port of the pouch of FIG. 3, and the first connector capable of forming a fluid-tight connection with a second connector of the apparatus of FIG. 1.

The barcode reader 19 may comprise any suitable barcode reading device now known or later developed that is capable of reading barcodes present on an external surface of components such as, for example, the first connector 13, the second connector 15, the pouch 30 (FIG. 3), the formulation receiving chamber 20 (FIG. 2), and/or a connecting conduit (FIG. 4). By scanning and recording the barcodes of each component in the system, proper connections may be automatically controlled by the controller. The barcodes may be in the form of a label attached to the components; alternately, the barcodes may be molded onto the components during their manufacture. The connecting device 16 is coupled with the barcode reader 19 so that that the controller may coordinate automatic reading of the barcode on each component entering and leaving the system.

Referring now to FIG. 3, pouch 30 contains a substance that is an ingredient of the intended formulation. Exemplary such pouches are disclosed in the following co-pending patent application, which is hereby expressly incorporated by reference as part of the present disclosure: U.S. patent application Ser. No. 14/990,778, filed Jan. 7, 2016, entitled "Pouch with Sealed Fitment and Method", which claims the benefit of similarly titled U.S. Provisional Application No. 62/100,725, filed Jan. 7, 2015, each of which is hereby expressly incorporated by reference in its entirety as part of the present disclosure as if fully set forth herein.

In the exemplary embodiment shown in FIG. 3, the pouch 30 includes a dispensing port 33, and a filling port 35. An exemplary connector for connecting to the dispensing port 33 includes connector 41 shown in FIG. 4, and the connectors are disclosed in the U.S. Provisional Application entitled "Single Use Connectors" filed on even date herewith, which is hereby expressly incorporated by reference as part of the present disclosure. In the exemplary embodiment shown in FIG. 3, the pouch is filled with a substance 31. In one embodiment, the substance 31 may comprise sterile or purified water for water fall injection (WFI). In alternate embodiments, the substance 31 may be any component or ingredient of a formulation or product. In the illustrated embodiment, pouch 30 may be filled through a penetrable and resealable septum 37 overlying the filling port 35, the septum 37 being in fluid connection with an internal chamber of the pouch 30. The dispensing port 33 may also include a penetrable septum in fluid connection with an internal chamber of the pouch 30, which may be penetrated by a connector, e.g., connector 41 to place a fluid conduit, e.g., conduit 18, in fluid communication with the substance 31 for dispensing through the conduit 18. The septums of the ports 33, 35 maintain the interior of the pouch 30 hermetically sealed from the ambient atmosphere. Alternatively, the dispensing port 33 and/or filling port 35 may include a valve or other device that maintains interior of the pouch 30 in sealed condition but allows a connector to be placed into fluid communication therewith. In one embodiment, the pouch 30 may include barcodes readable by a barcode reader, such as the barcode reader 19 (FIG. 1).

Prior to filling the pouch with substance 31, the pouch 30 and the pouch's internal and/or external surfaces may be sterilized. The apparatus and methods for sterilizing the pouch and its external surfaces may take the form of any of the apparatus and methods disclosed in the following commonly assigned patents and patent applications which are hereby expressly incorporated by reference as part of the present disclosure: U.S. patent application Ser. No. 10/766,172, filed Jan. 28, 2004, entitled "Medicament Vial Having A Heat-Sealable Cap, And Apparatus and Method For Filling The Vial", which is a continuation-in-part of similarly titled U.S. patent application Ser. No. 10/694,364, filed Oct. 27, 2003, which is a continuation of similarly titled co-pending U.S. patent application Ser. No. 10/393,966, filed Mar. 21, 2003, which is a divisional of similarly titled U.S. patent application Ser. No. 09/781,846, filed Feb. 12, 2001, now U.S. Pat. No. 6,604,561, issued Aug. 12, 2003, which, in turn, claims the benefit of similarly titled U.S. Provisional Application Ser. No. 60/182,139, filed Feb. 11, 2000; and U.S. Provisional Patent Application No. 60/443,526, filed Jan. 28, 2003; and similarly titled U.S. Provisional Patent Application No. 60/484,204, filed Jun. 30, 2003; U.S. patent application Ser. No. 10/655,455, entitled "Sealed Containers And Methods Of Making And Filling Same", filed Sep. 3, 2003, which, in turn, claims the benefit of similarly-titled U.S. Provisional Patent Application No. 60/408,068 filed Sep. 3, 2002; U.S. Provisional Patent Application No. 60/551,565, filed Mar. 8, 2004, titled "Apparatus and Method for Molding and Assembling Containers with Stoppers"; U.S. patent application Ser. No. 10/600,525 filed Jun. 19, 2003 titled "Sterile Filling Machine Having Needle Filling Station Within E-Beam Chamber", which, in turn, claims the benefit of similarly-titled U.S. Provisional Application No. 60/390,212 filed Jun. 19, 2002; U.S. patent application Ser. No. 10/983,178 filed Nov. 5, 2004 titled "Needle Filling and Laser Sealing Station", which, in turn, claims the benefit of similarly-titled U.S. Provisional Patent Application No. 60/518,267 filed Nov. 7, 2003 and similarly-titled U.S. Provisional Patent Application No. 60/518,685 filed Nov. 10, 2003; U.S. Provisional Patent Application No. 60/550,805 filed Mar. 5, 2004 titled "Apparatus for Needle Filling and Laser Resealing"; and U.S. patent application Ser. No. 08/424,932 filed Apr. 11, 1995 now U.S. Pat. No. 5,641,004 issued Jun. 24, 1997 titled "Process for Filling a Sealed Receptacle Under Aseptic Conditions."

Referring now to FIG. 4, connecting conduit 40 represents a conduit through which sterile transfer of the substance 31 (FIG. 3) occurs. As shown in FIG. 4, one end of the connecting conduit terminates in a connector 41 while the other end terminates in the first connector 13, with the channel 18 fluidically connecting the two connectors. In one embodiment, the first connector 13 may comprise a sterile male connector that forms a fluid-tight hermetic seal with the second connector 15 of FIG. 1, or with second connectors 15a, 15b, and 15c shown in FIG. 2.

Referring now to FIG. 2, formulation-receiving chamber 20 may be a sterile and/or closed to the ambient atmosphere, and may include second connectors 15a, 15b, and 15c, and third connector 25, with each of these connectors in fluid communication with the formulation chamber. In one embodiment, the formulation chamber 20 may comprise a large blending tank or a blending pouch into which ingredients may be introduced to produce a formulation therein. The second connectors 15a, 15b, and 15c may be similar in structure and function to the first connector 13 or the second connector 15 described with reference with FIG. 1. The formulation chamber 20 may receive substances via the connectors 15a, 15b 15c, and 25 with substances received into and mixing or blending within the chamber. For each connection, the flow rate of each of the substances is measured by a device (in communication with the controller) such as described above with reference to FIG. 1. The time the connection is its connected state may also be recorded by the controller, e.g., based on signals from the connecting device 16 that a connection or disconnection has been made. Accordingly, based on the measured flow rate and connection time, the controller can determine the volume of the materials that has been transferred through the connection, e.g., into the formulation chamber 20.

The substances transferred into the formulation chamber 20 may be of any material suitable for such transfer. In one embodiment, formulation chamber 20 may be prefilled with a substance that occupies a portion of the formulation-receiving chamber. In one embodiment, this substance may represent a powder ingredient that forms part of the final formulation.

The controller may control transfer of substances from one or more pouches 30 or other substance sources, with substance flow from each and into the formulation-receiving chamber 20 being regulated by the device 10, as follows. The controller may initiate a fluid-tight hermetic connection of the connector 41 of the connecting conduit 40 with the dispensing port 33 of the pouch 30, the pouch 30 containing a substance that is an ingredient of the intended formulation to be formed within the formulation chamber 20. The controller may then signal the connecting device 16 of the device 10 to connect, e.g., form a fluid-tight hermetic seal between, the first connector 13 located at the other end of the connecting conduit 40 and the second connector in fluid connection with the receiving chamber. The PLC controller may further signal the barcode reader to read and transmit the barcodes of the pouch, the first connector, the second connector, and optionally the pouch, e.g., in order to determine what substance is being transferred through what connection. After a fluid tight hermetic seal is formed between the first and second connectors, transfer of the substance from the pouch takes place, through the connecting conduit 40 and into the fluid receiving chamber 20. In one embodiment, the PLC controller may signal a pump (not shown) to pump the material from its source and into the formulation chamber 20. In one embodiment, this pump comprises a peristaltic pump. The peristaltic pump prevents any contact between pump parts and the substance being transferred. Using a peristaltic pump for pumping thus eliminates the need to sterilize the pump prior to use, or to clean or re-sterilize the pump after completion of a sterile transfer or before a change in the substance being transferred into the formulation-receiving chamber.

The controller may further signal the flow meter 11 to measure and transmit one or more of a time, flow rate, or a volume of the substance being transferred. Alternatively, the flow meter 11 may transmit such information without receiving such a signal from the controller. The flow meter 11 may be configured to measure the flow rate at or near a barcoded component. The controller may then compare the measured time, flow rate, and/or volume with a predetermined time, flow rate and/or volume. Based on the comparison, the controller may adjust one or more of the time, flow rate (e.g., by controlling a pump or valve) or the volume of the transfer of a given substance to provide a predetermined formulation in the formulation receiving chamber. For example, the controller may signal the connecting device 16 to disconnect the connectors 13, 15 after a certain time of connection or volume of transfer in order to cease the flow of substance to the formulation chamber 20.

The controller may also record and store residence time and distribution of each step of the processing and may automatically control the consistency of the time the flow connection is made (time of connection) and of the flow rates resulting in consistent transfer/blending processing, thereby enabling continuous manufacturing of fluid formulations. Using this method, the quality and consistency of the manufactured formulation formed of different mixed components can be measured and controlled by controlling the time the flow connection is made for each substance being transferred into the formulation chamber 20. In other words, the precise amount and proportion of the various constituent substances can be precisely controlled, and documented, to ensure high quality, e.g., compliance, and/or consistency of the resulting formulation. This method may thus result in a reproducible and sustainable formulation process by which sterility and particle-free nature of resulting formulation may be achieved. In some embodiments, due to the closed construction of the system and use of sterile connectors to make connections in the system, this may be accomplished in Controlled Non-Classified (CNC) or even a non-classified environment.

Upon completion of transfer of substance from each pouch or substance source, the second connector 15 is disconnected from formulation receiving chamber. The connecting conduit 40 along with the pouch 30 to which the connector end 41 of the connecting conduit 40 is attached may be discarded. Single use of these components may help to avoid cross-contamination.

The apparatus and methods for sterilizing the pouch and its external surfaces may take the form of any of the apparatus and methods disclosed in the following commonly assigned patents and patent applications which are hereby expressly incorporated by reference as part of the present disclosure: U.S. patent application Ser. No. 10/766,172, filed Jan. 28, 2004, entitled "Medicament Vial Having A Heat-Sealable Cap, And Apparatus and Method For Filling The Vial", which is a continuation-in-part of similarly titled U.S. patent application Ser. No. 10/694,364, filed Oct. 27, 2003, which is a continuation of similarly titled co-pending U.S. patent application Ser. No. 10/393,966, filed Mar. 21, 2003, In alternative embodiments, rather than using barcodes and barcode readers, or in addition thereto, one or both of the connector halves 13, 15 may include a radio frequency identification (RFID) tag or chip that, in a manner that should be understood by those of ordinary skill in the art, uniquely identifies the connector and/or connector halves. An RFID tag reader may be utilized, in a manner that should be understood by those of ordinary skill in the art, to "read" the RFID tag. The reader may then transmit the identifying information to the controller 11a to be utilized in a similar manner as the information provided by the barcodes and barcode reader. One difference between barcoding and using RFID tags is that barcoding requires a line-of-sight between the barcode and the barcode reader, and the environmental conditions must be suitable for the reader to read the barcode, e.g., sufficient light, clarity, etc. Another difference is that the RFID tags use a local power source, such as a battery. Though currently-known RFID tag power sources may provide sufficient power to the tag for extended periods of time, e.g., years, at some point the power source needs to be replenished/recharged or replaced, or the RFID tag itself replaced. Thus, as will be appreciated by those of ordinary skill in the art, in some systems of the invention it may be more advantageous to use barcodes/barcode readers and in other systems RFID tags/readers. It should also be understood that yet other types of identification systems, either currently-known or later developed, may be used to identify a connector or connector portion.

The above-described method may enable manufacturing formulations that include fewer particulates in the final formulation than what is possible by mere closing of a cap onto an open formulation-receiving chamber as is done in traditional aseptic transfer processes. Traditional aseptic transfer processes often rely on the cleanliness of the manufacturing environment and the lack of particulates presence in the ambient atmosphere in which the open receiving chambers are filled (controlled environment for pharmaceutical production) to reduce contamination and to maintain sterility.

The formulation chambers 20 may be closed within the mold or right after molding under microfiltered laminar airflow that may contain a very low level of particulates. The closed receiving chambers 20 may then be sterilized while closed by known methods, such as, for example, by irradiation. This approach may result in extremely limited amount of small particles, if any, and germ-free conditions within the receiving chamber 20 as well as the manufactured formulation. The resulting formulation may be safer for patient use than traditional pharmaceutical processing carried out in a controlled environment. Thus, the method may, in addition to improving the purity and sterility of the manufactured formulation, also result in improved quality and consistency of the resulting formulation when compared to traditional manufacturing.

The method and apparatus described herein may thus control sterile transfer of substances during the manufacture of a predetermined formulation, the method including a controller measuring one or more of a timing or a volume of sterile transfer of the substance to measure a residence time of the substance at each stage of the transfer process and adjusting one or more of the timing or the volume of the sterile transfer to manufacture the predetermined formulation.

The systems and methods of the invention rely on certain conditions. First, the connector portions should be properly connected to avoid leakage and/or ingress of air, microbes or other contamination. In addition, the connector should be in a position in which identifier for the connector or connector portion(s) (e.g., barcode, RFID tag, etc.) can be read or determined (e.g., by a barcode reader, RFID tag reader, etc.). Further, the flow meter should be in a position relative to a flow conduit of or in fluid communication with the connector so that it can accurately measure the flow therethrough. If any of these conditions are not present, the system may not properly function or the system may not assure the resulting formulation.

Figure 5:
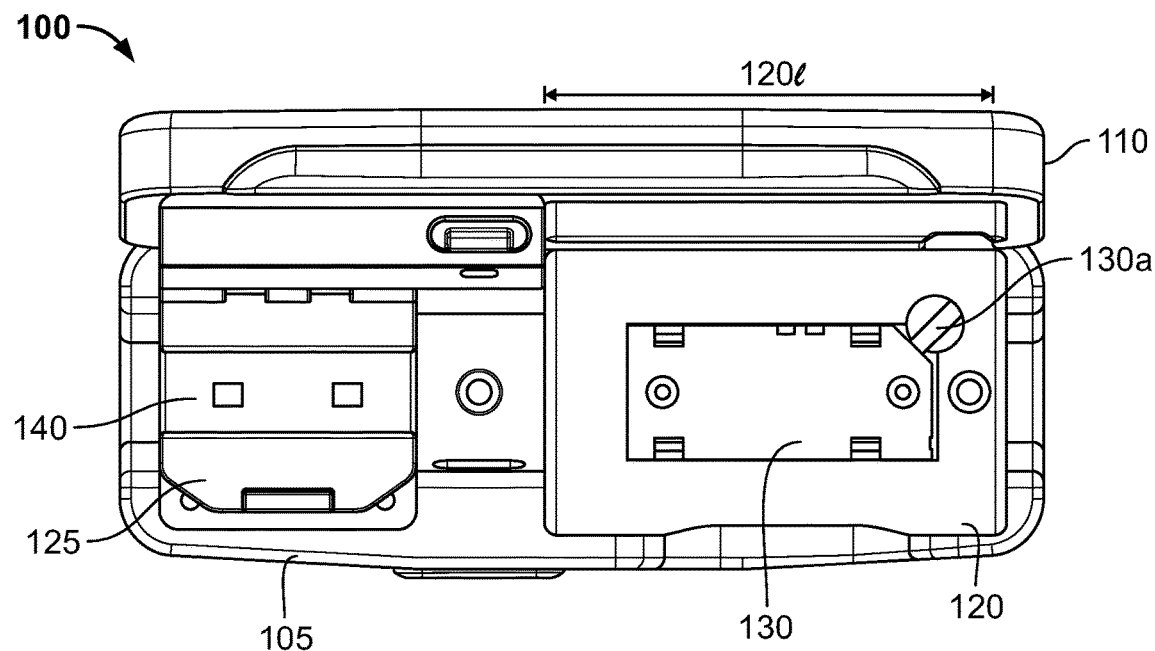
FIG. 5 is a top view of a cradle with the cover of the cradle in an open position.
Figure 6:
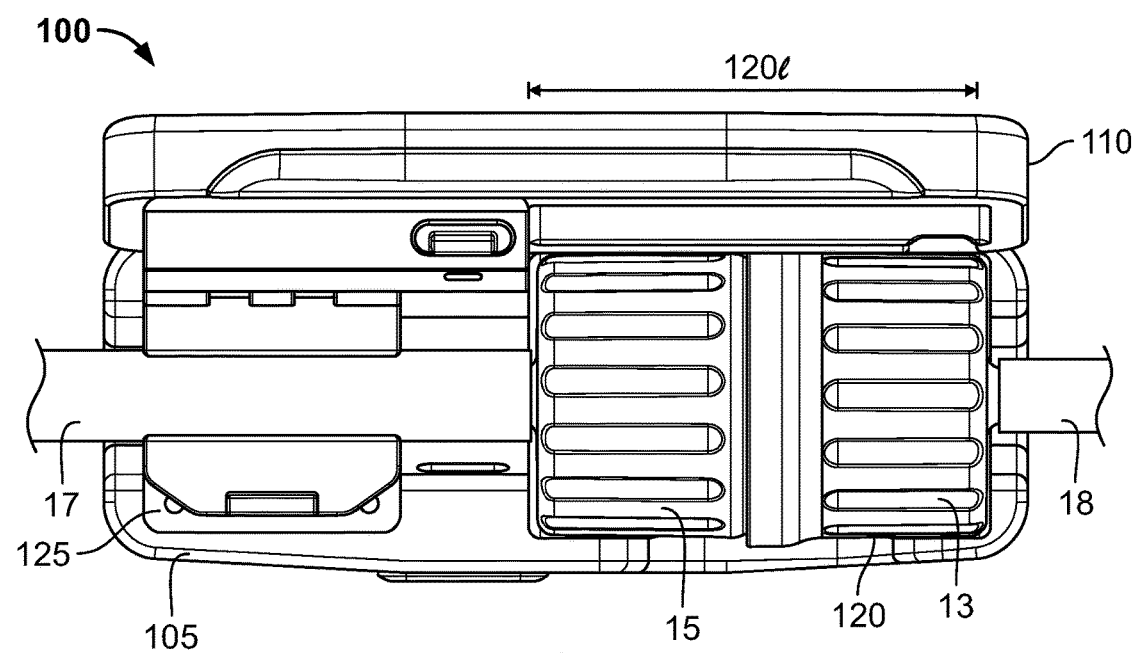
FIG. 6 is a top view of the cradle of FIG. 5 with a connector located therein.
Figure 7:
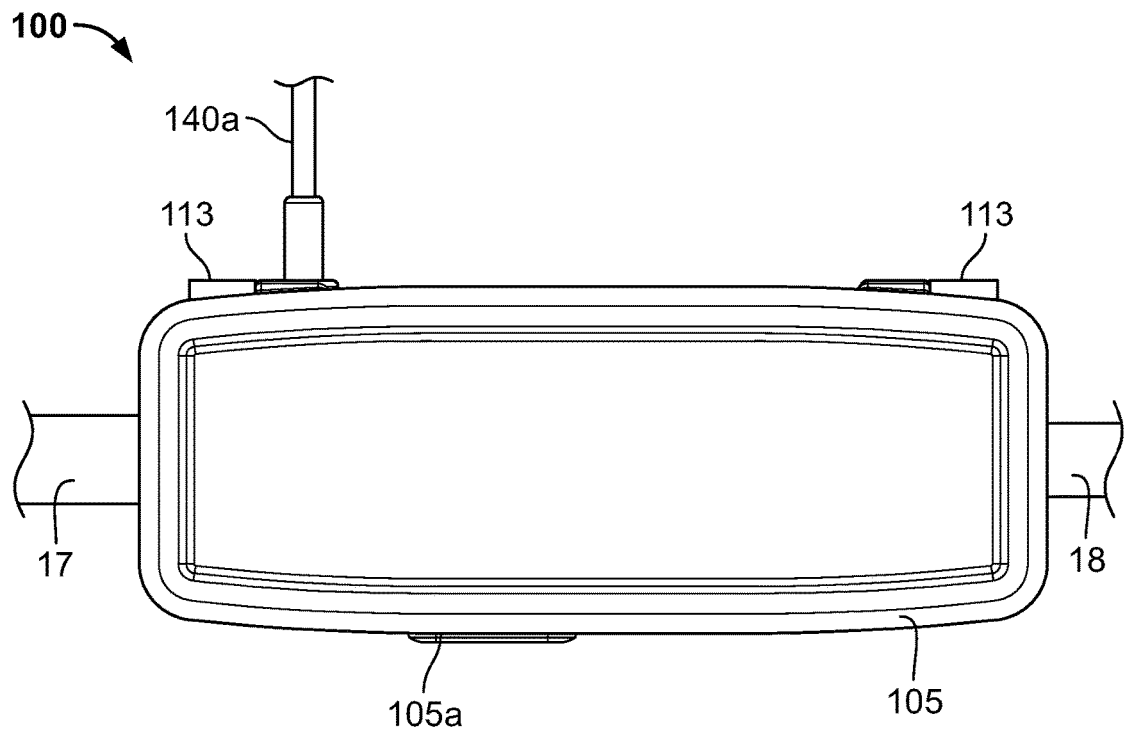
FIG. 7 is a top view of the cradle of FIG. 6 with the cover of the cradle in a closed position.
Figure 8:
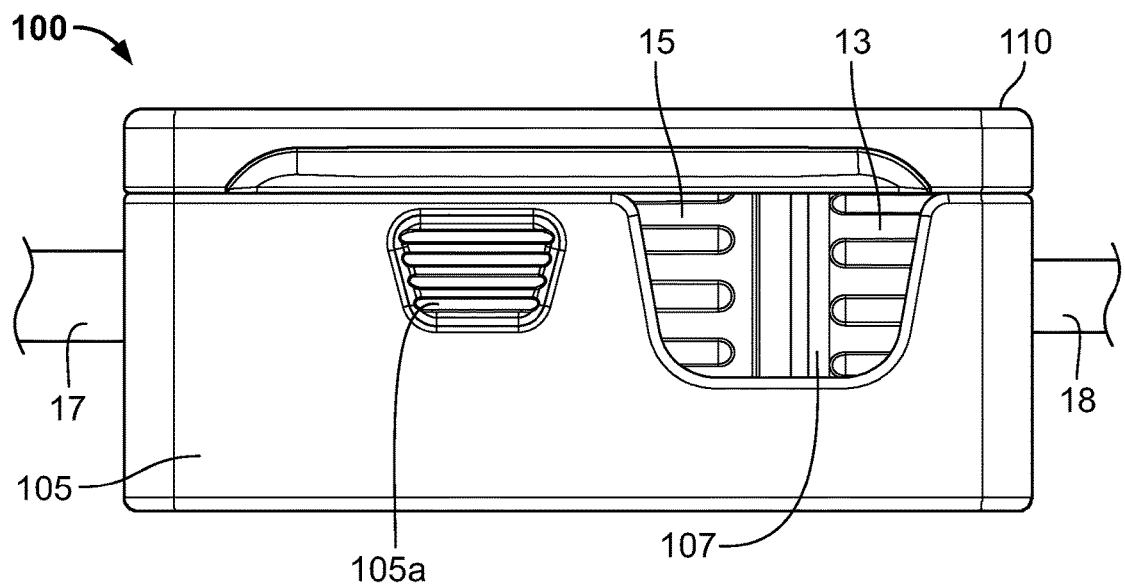
FIG. 8 is a front view of the cradle of FIG. 7.

Referring to FIGS. 5-8, a cradle or holder 100 can be utilized to help ensure the above conditions. Cradle 100 has a main body 105 and a door or cover 110 movable relative to the body 105 between an open position as shown in FIGS. 5 and 6, to a closed position as shown in FIGS. 7 and 8. In the illustrated embodiment, the cover 110 is pivotably connected to the main body 105 by hinges 113. In other embodiments, the cover 110 is attached to the body 105 by mechanisms other than hinges, which should be recognized by those of ordinary skill in the art. In yet other embodiments, the cover 110 is not fixedly attached to the body 105.

The main body 105 defines a first interior cavity 120 and a second interior cavity 125. The first interior cavity 120 is sized and shaped to receive therein a connector when the connector halves 13, 15 are in the connected position. More specifically, the first interior cavity 120 defines a length 1201 that permits the connector to be received in the first cavity 120 only when the connector halves 13, 15 are in the properly connected. If the connector halves 13, 15 are not properly connected together, the overall length of the connector will exceed the length 1201 of the first interior cavity 120, and the connector will not fit into the interior cavity. In this regards, the first interior cavity 120 ensures that the connector is properly connected to avoid leakage of contamination.

The first interior cavity 120 also contains a reader or sensor 130 configured to identify the connector and/or connector halves 13, 15 present in the interior cavity as discussed above. In some embodiments, the sensor is an RFID tag reader adapted to read the RFID tag(s) present on the connector. In other embodiments, the sensor 130 is a barcode reader that is configured to read the barcode(s) on the connector. When the sensor 130 determines the identifying information regarding the connector and/or connector halves 13, 15, it transmits that information to the controller 11a via wire 130a. In other embodiments, the identifying information is transmitted wirelessly, as would be understood by those or ordinary skill in the art. The controller 11a may then use the identifying information to control fluid flow through the connector, and according, the formulation process, as described herein. In some embodiments, wire 130a supplies electrical power to the sensor 130. In other embodiments, the sensor 130 is locally powered, such as by a battery.

The second interior cavity 125 is sized and configured so as to be able to receive therein a portion of the flow channel 17 of the connector, e.g., a tube or conduit. The second interior cavity contains therein a flow meter 140. The flow meter 140 is located with the second interior cavity 125 and otherwise configured so that, when the connector is located in the cradle, and thus a portion of the flow channel 17, the flow meter 140 can measure or otherwise determine the flow rate of substance through the connector as described herein. In the illustrated embodiment, the flow meter 140 transmits its readings to controller 11a via wire 140a. In other embodiments, the cradle 100 is wirelessly enabled in a manner that should be understood by those of ordinary skill in the art, for wireless transmission of the flow reading to the controller 11a. In some embodiments, wire 140a supplies electrical power to the flow meter 140. In other embodiments, the flow meter 140 is locally powered, such as by a battery.

As seen in FIGS. 5 and 6, when the cover 110 is in the open position, the cover 110 does not block ingress or egress of the connector or the flow channels 17, 18 into or out of the interior cavities. The connector and a portion of the flow channel 17 may then be inserted into the cradle, e.g., the first and second cavities 120, 125, respectively. Once the connector and flow channel 17 are placed within the cradle 100, the cover 110 may be closed as shown in FIGS. 7 and 8.

When the cover 110 is closed, the cover 110 sufficiently blocks access to the interior cavities 120, 125 so that the connector and/or flow channel 17 may not be removed from the cradle 100. Thus, the cover 110 help prevent inadvertent removal or dislodging of the connector and/or flow channel 17 from the first and second cavities 120, 125, respectively, that may interfere with the readings of the sensor 130 and/or flow meter 140, and consequently the operation of the formulation system and/or the quality and content of the formulation.

In the illustrated embodiment, the cradle 100 contains a latching system that releasably retains the cover 110 in the closed position to help prevent inadvertent opening of the cover 110. Cover 110 contains a latch 110a that engages the main body 105 to retain the cover 110 in the closed position. Main body 105 has a depressible release 105a that, in a known fashion, disengages the latch 105a from the main body 105 to allow the cover 110 to be moved toward the open position. Those skilled in the art will understand that other latching systems alternatively may be utilized in the invention.

Figure 9:
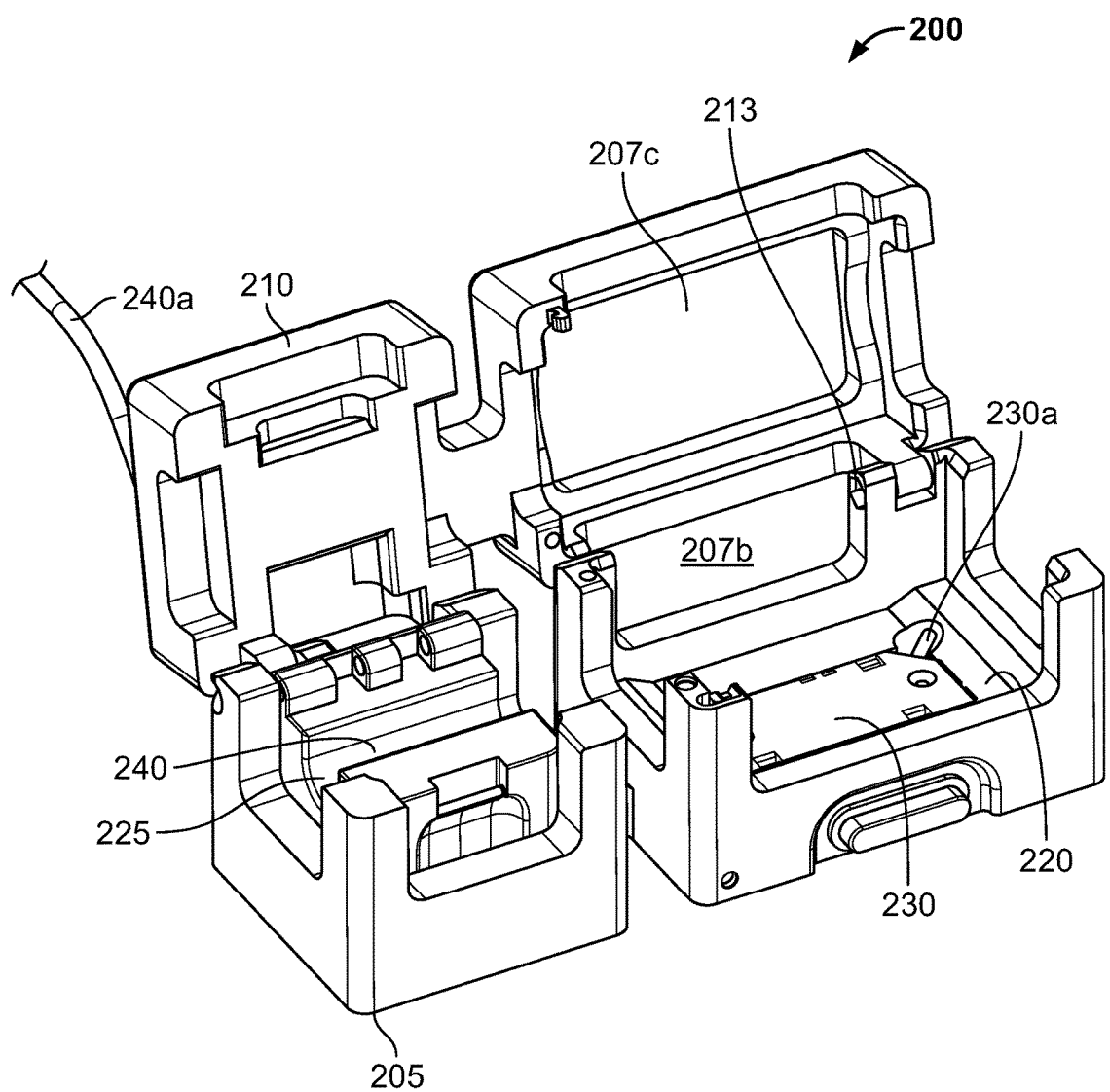
FIG. 9 is a top perspective view of another embodiment of a cradle with the cover of the cradle in an open position.
Figure 10:
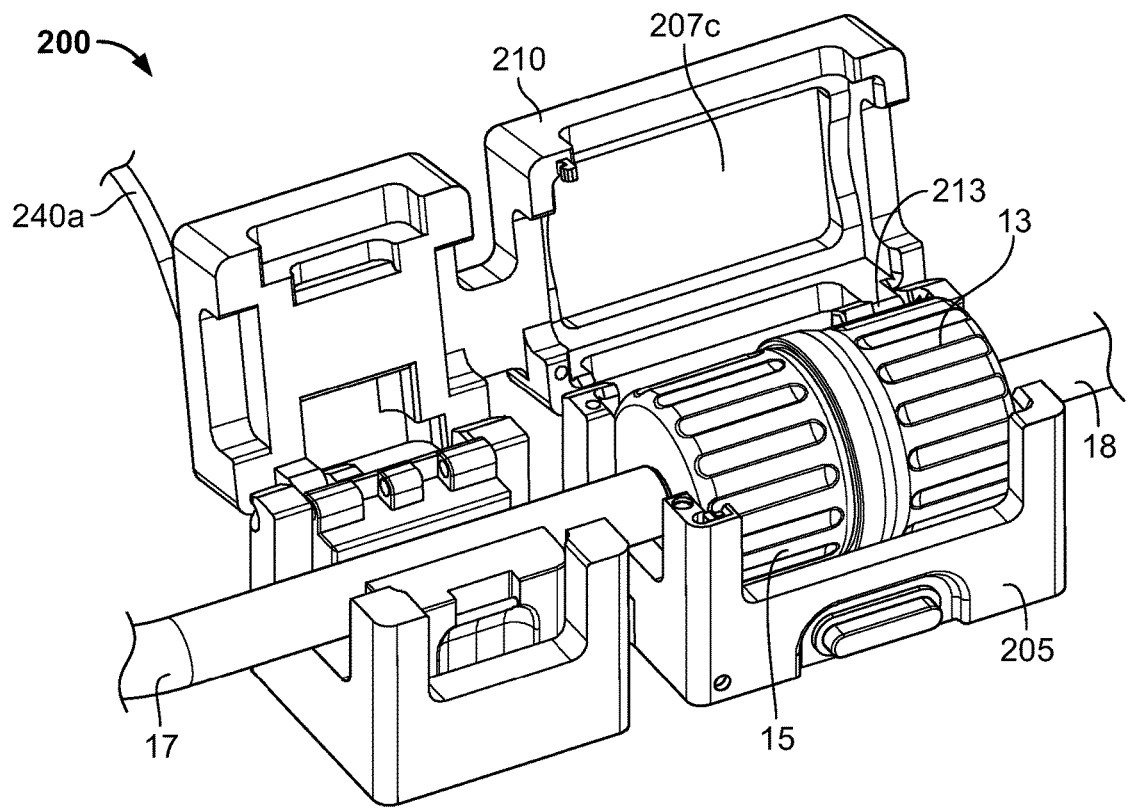
FIG. 10 is a top perspective view of the cradle of FIG. 9 with a connector located therein.
Figure 11:
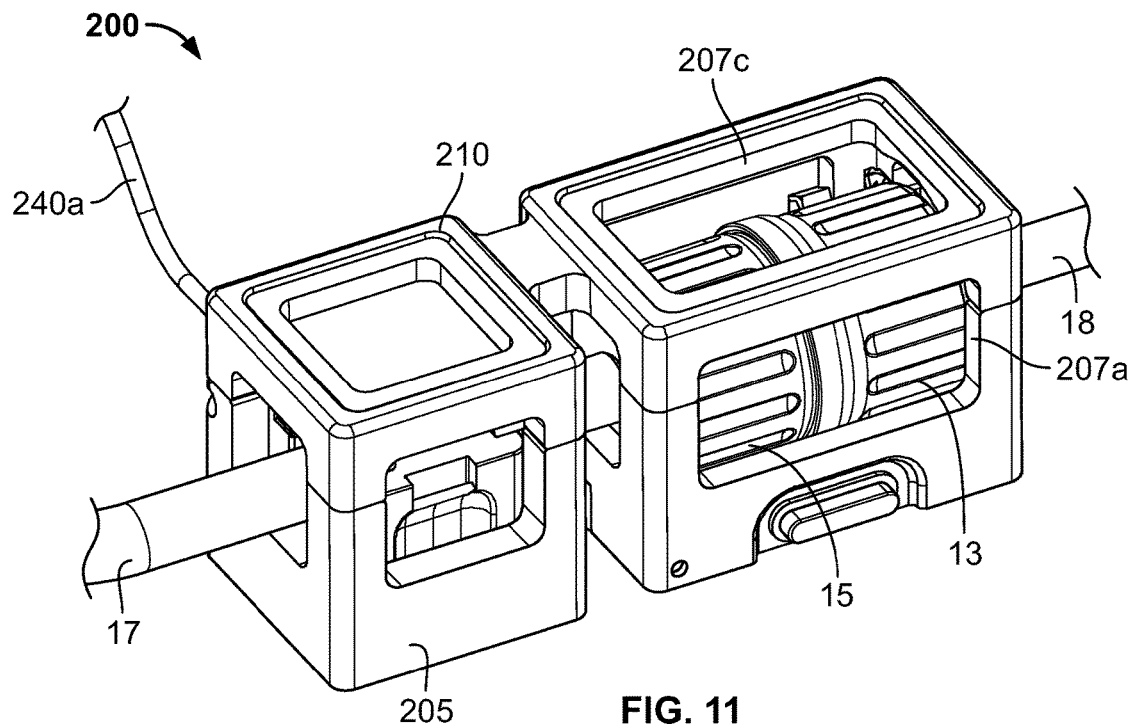
FIG. 11 is a top perspective view of the cradle of FIG. 9 with the cover of the cradle in a substantially closed position.

Referring now to FIGS. 9-11, another embodiment of cradle 200 is shown. Cradle 200 is similar to cradle 100 in a number of respects, and like elements use like reference numbers, but are preceded with the numeral "2" instead of the numeral "1" as used in FIGS. 5-8. Like cradle 100, cradle 200 contains a main body 205 and a cover 210 that is pivotably connected to the main body 205 via hinge connection 213. Cradle body 205 defines a first interior cavity 220 and a second interior cavity 225 for receiving therein a connector and a flow channel 17, respectively. The first interior cavity 220 includes a reader or sensor 230 that is configured and functions similarly to sensor 130 of cradle 100. The second interior cavity 225 includes a flow meter 240 that is configured and functions similarly to flow meter 140 of cradle 100. In addition, embodiments of cradle 200 can include similar safety and/or interlock features as may cradle 100.

One way in which cradle 200 differs from cradle 100 is that instead of defining only one viewing window, body 205 defines three viewing windows 207a, 207b, 207c. Another way in which cradle 200 differs from cradle 100 is that cradle 200 does not have a latching mechanism. Other differences between cradle 100 and cradle 200, including but not limited to the shape and configuration of the cradles, should be apparent from the figures to those of ordinary skill in the art.

Figure 12:
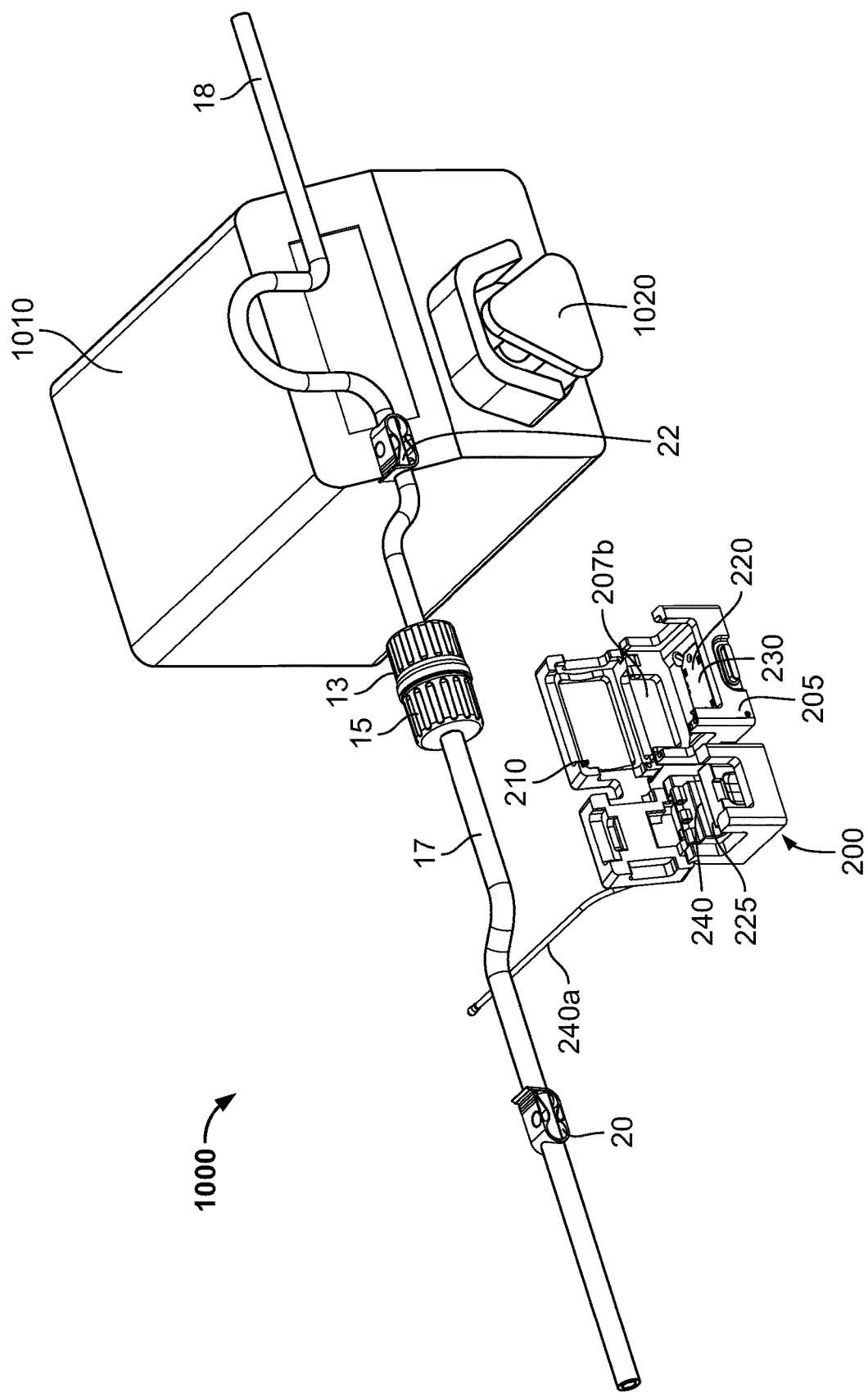
FIG. 12 is a front perspective view of a system including a pump, a connector in a connected position, and the cradle of FIGS. 9-11 with the cover in an open position.
Figure 13:
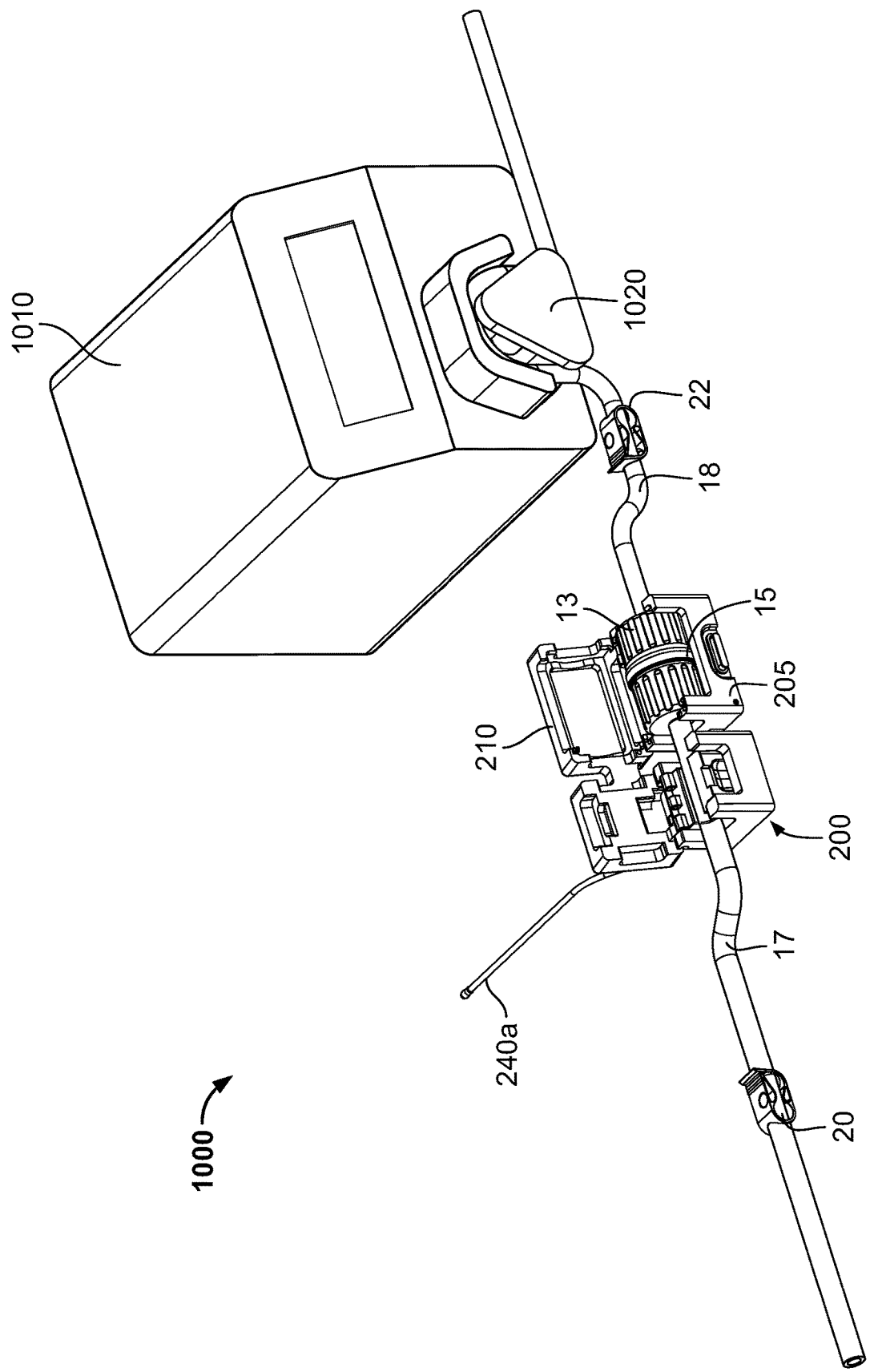
FIG. 13 is a front perspective view of the system of FIG. 12 with the connector inlet tubing engaged with the pump and the connector located in the cradle with the cover in an open position.
Figure 14:
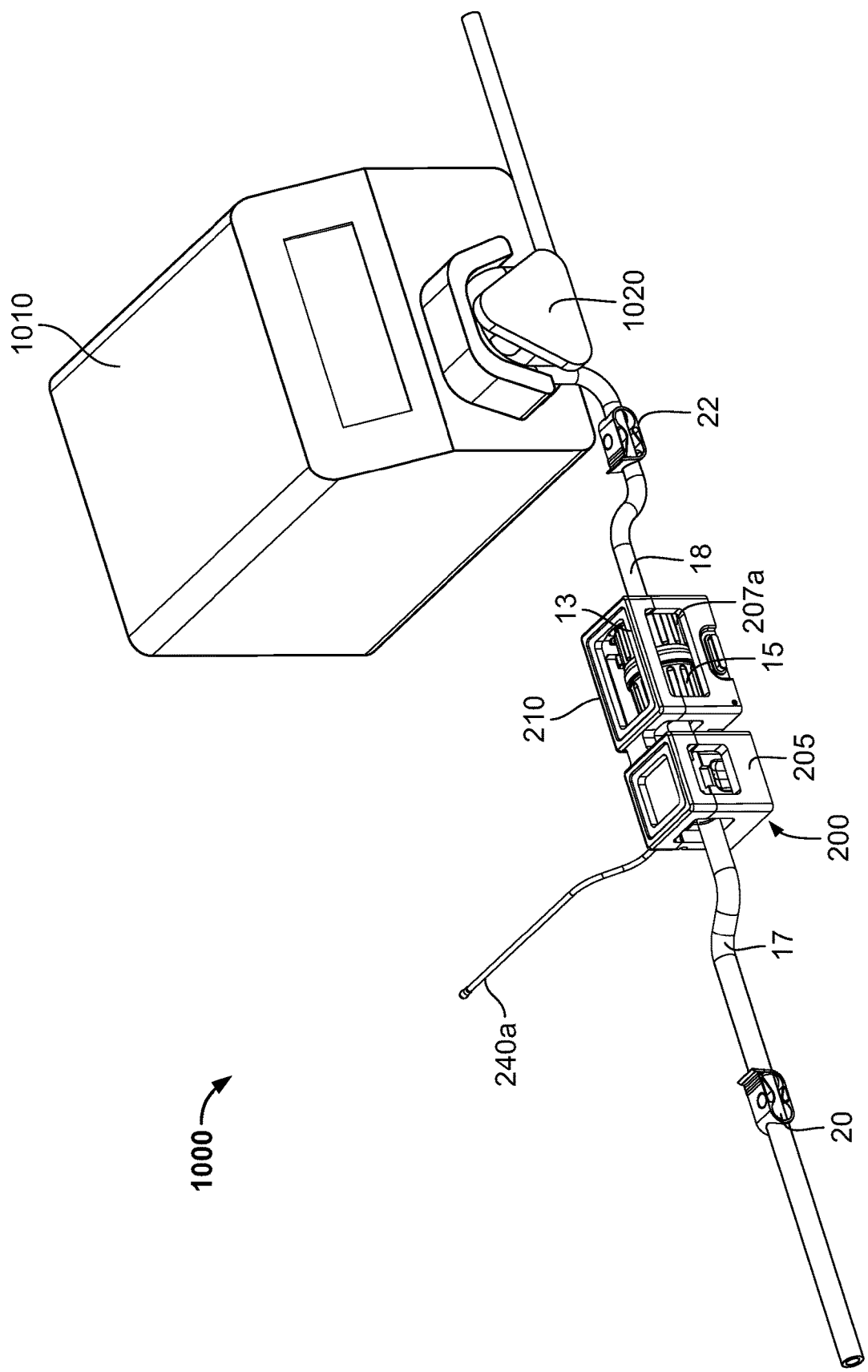
FIG. 14 is a front perspective view of the system of FIG. 13 with the cover in a closed position.

FIGS. 12-14 schematically illustrate an exemplary use of the cradle 200 in a formulation system 1000. In addition to the cradle 200 and the connector (portions 13, 15 and flow channels 17, 18 in fluid communication thereof), the system 1000 include a pump 1010 including a pumping mechanism configured to pump substance in flow channel 18 (e.g., a tube or conduit) through the connector and subsequently along flow channel 17. In the illustrated embodiment, the pump 1010 is a peristaltic-type pump, as is known. In such pumps, the pumping mechanism 1020 engages the external surface 18a of the flow channel 18, and by a sequential compression/squeezing action by the pumping mechanism 1020 on the external surface 18a, compresses the substance in the flow channel 18 and thereby pumps the substance. Peristaltic-type pumps may be used in closed or intact systems in which the pumped substance does not contact or become exposed to the ambient atmosphere. No part of the pump 1010 contacts the substance itself in the flow channel 18, reducing risk of contamination of the substance. In contrast, pumps whose parts contact the pumped substance must rely on seals to prevent exposure of the substance to the ambient atmosphere or contaminants from the ambient atmosphere. Such seals can fail, leading to undesirable exposure or contamination of the substance.

In addition, flow channels 17, 18 contain flow control valves or clips 20, 22, respectively, that can control flow through the flow channels 17, 18 independently of the operation of the pump 1010. In some embodiments, the flow channels 17, 18 are flexible tubing. The clips 20, 22 may each be manually adjusted to at least partially and/or fully crimp or squeeze down the flow channels 17, 18 to restrict or stop flow through a respective flow channel. The illustrated clips 20, 22 contact only the exterior of the flow channels 17, 18, so that the clips 20, 22 do not contact the substance in the flow channels 17, 18, reducing the risk of contamination of the substance. It should be understood by those of ordinary skill in the art, though, that the illustrated flow control valves are merely exemplary, and any suitable valve(s), that either contact the substance in the flow channels 17, 18 or not, may be used.

As seen in FIG. 12, the connector halves 13, 15 have been connected together forming a fluid path between flow channels 17 and 18 through the connector. The halves 13, 15 can be connected by various ways. They can be manually connected. The may alternatively be connected by a connecting device, such as connecting device 16 described above. The cover 210 of the cradle 200 is in the open position, permitting access to the first and second interior cavities 220, 225. As seen in FIG. 13, the connector has been placed into the cradle 200, with the connector located in the first interior cavity 220, and the flow connector 17 located in the second interior cavity 225. In addition, the flow channel 18 has been placed into engagement with the pumping mechanism 1020 of the pump 1010. Though, as illustrated, the flow channel 18 has been engaged with the pump, in other embodiments flow channel 17 may be engaged with the pump 1010. Turning now to FIG. 14, the cover 210 has been moved to the closed position. The connector is accordingly retained in the cradle 210 for formulation operations and monitoring and recording by the controller 11a. In some embodiments, the cover 210 is configured to place a compression force on the connector and flow channel 17 in the closed position, so as to further maintain the components in the proper position.

The cradle 200 may provide or utilize one or more safety features or interlocks to help assure that the formulation processing system does not operate under unfavorable conditions. More specifically, the cradle 200 may contain systems that ensure that substance is not transferred though the connector if one or more desired conditions are not present. For example, sensor 230 may be utilized as a connector presence detector. If the reader 230 does not or cannot read the barcode(s), RFID tag(s), or other identifier(s) of a connector, this may indicate that the connector is not properly positioned in the cradle 200. As described above, if the connector is not properly positioned in the first interior cavity 220, a proper connection of the connector halves 13, 15 cannot be verified. In that case, where the sensor does not read or determine the identifying information, the sensor 230 will not transmit any identification information to the controller 11a. In such embodiments, the controller 11a may be programmed to determine that, in the absence of receiving identifying information from the reader 230, the connector portions 13, 15 may not be properly connected. In these circumstances, the controller 11a may not operate the system, e.g., activate the pump 1010, or otherwise operate the formulation processing a revise manner. Accordingly, leakage and/or contamination of substance transferred through the connector can be effectively avoided.

In other embodiments, the first interior cavity 220 may contain another or additional presence sensor. In some embodiments, the presence sensor may be mechanical or electromechanical, such as a switch that is configured and placed in the cradle so as to be moved from a first position when the connector is not properly located in the first interior cavity 220 to a second position when the connector is properly located in the first interior cavity 220. In the second position, the switch may transmit a signal to the controller 11a, which the controller 11a recognizes as indicating that the connector is properly located in the first interior cavity 220. In the first position, the switch may transmit a signal to the controller 11a that the controller 11a recognizes as indicating that the connector is not properly located in the first interior cavity 220. Alternatively, in the first position, the switch may transmit no signal to the controller 11a, which the controller 11a recognizes as indicating that the connector is not properly located in the first interior cavity 220. The switch may be biased toward the first position, e.g., by a spring, so that the default indication to the controller 11a is that the connector is not properly present in the cradle 200.

In other embodiments, the connector presence detector may be electronic, such as, for example, an "electric eye." As should be understood by those in the art, an electronic connector presence detector could operate similarly to the mechanical or electromechanical detector in that if the detector does not detect the connector in the proper position in the cradle 200, it may send a signal or no signal to the controller 11a that the controller will recognize as indicated that the connector is not properly positioned in the first interior cavity 220. Conversely, if the detector detects the connector in the proper position, it may send a signal to the controller 11a that is recognized as indicating that the connector is properly positioned in the first interior cavity 220.

Those skilled in the art should recognize that other systems for determining whether the connector is properly located within the cradle 200. In all these embodiments, though, if the controller 11a does not receive a signal indicating that the connector is properly located in the first interior cavity 220, or if the controller 11a ceases to receive such a signal, the controller 11a may prevent the system from operating, e.g., not operate or shut down the pump 1010, or otherwise stop or modify the operation of the formulation system to compensate.

As seen in FIGS. 9-14, the main body 205 also defines an opening or viewing windows 207a, 207b, 207c that permits viewing of the connector in the first interior cavity 220. This permits visual confirmation of that the connector is properly located within the first interior cavity. Other embodiments, though, do not have a viewing window.

In yet other embodiments, the cradle 200 includes a cover position detector. The cover position detector detects whether the cover 210 is in the open position or the closed position. Similar to the connector presence detector, the cover position detector may utilize mechanical, electromechanical and/or electronic systems to determine the position of the cover 210. For example, a switch may be configured and placed in the cradle 200 so as to be moved from a first position when the cover 210 is open (or not closed) to a second position when the cover is in the closed position. In the first position, the controller 11a receives a signal or receives no signal from the cradle 200, which the controller 11a recognizes as indicating that the cover is open or not closed. In the second position, the controller 11a receives a signal that the cover is closed. If the controller 11a does not receive a signal that the cover is closed, the controller 11a may prevent the system from operating, cease operation of the system, and/or modify system operation to compensate for that closure of the cover is not confirmed. The switch may be biased toward the first position, e.g., by a spring, so that the default indication to the controller 11a is that the cover is in the open position. Accordingly, any disconnection of the connector hales 13, 15 would require opening of the cover and removing the connector from the cradle, one or both of which events would be recognized and/or recorded by the controller 11a, which may execute appropriate actions.

It should be noted that in embodiments where the flow path of the substance is closed or sealed from the ambient atmosphere, e.g., the substance does not contact or become exposed to the ambient atmosphere or environmental contaminants as it flows through he flow channels 17, 18 and the connectors, the cradles or holders of the invention may be used in a non-classified environment. This is accomplished because the substance does not contacting at the readers, sensors, flow meters and other components of the cradles. All of the measuring, sensing, reading and detecting by the cradles is performed externally the connectors and flow channels 17, 18, preventing contamination of the substance by such components.

Accordingly, the invention effectively determines and assures a proper connection of the sterile connector before substance is passed through the connector. It also prevents uncontrolled human intervention and error in the production of a formulation. Thus, in combination with the aforesaid measurement and recording of substance transfer, flow timing, and residence time, by way of example, the invention enables high replication of product quality and composition among formulation lots, and also among different producers utilizing congruent formulation systems and process parameters.

The flow measurement capabilities of the invention also enable inventory management. By measuring the amount of ingredients used, the system can determine when ingredients run low or are depleted, or will become depleted. The controller 11a can then adjust the formulation process, e.g., batch size or flow rates of other ingredients, to prevent a deviation in formulation composition.

The invention also permits remote monitoring, inspection and auditing of the formulation process. The electronic transmission and recording of data from the sensors and flow meters permits an operator or auditor to monitor, review or analyze that process without being on-site at the production facility. This may be done based on recorded information that is retrieved by the operator. It may also be performed on a live update or real-time basis, with current process information sent to the auditor. If the reported information is within the desired or predetermined parameters, the auditor can be assured that the formulated product meets the product specifications. For example, if the flow rates and flow times of the various ingredients (and thus the ingredient amounts or relative ingredient amounts) meet the specifications, the formulated product will meet the specifications. Further, as the proper connection of the connectors can be verified by the cradle and recorded by the system, the auditor can be assured that the product meets quality requirements.

The invention thus enables the auditor to assess, control and/or verify that all the connections and the process in general all comply with requirements of process (according to the checklist used to assess compliance). Currently, regulations are general in nature and subject to interpretation by an auditor (e.g., the FDA). This is a somewhat subjective decision by the auditor, because the process parameters are presently not recorded. Thus, the auditor must assess, based on limited information, whether the regulations are complied with. In contrast, by using the invention, auditors may remotely determine compliance with regulatory requirements without an on-site visit, and without making subjective determinations based on limited information after-the-fact.

The invention may also be used to detect, mitigate and prevent errors. In addition to, as discussed above for example, preventing or modifying operation of the formulation process if a connector is not confirmed as being in the cradle and thus properly connected, the controller 11a, for example, compare current operating parameters against expected or specified operating parameters. If a deviation is detected, the controller 11a may modify current operation to return or maintain the product formulation to specification. For example, the controller can be configured (e.g., programmed) to compare measured ingredient flow rates against expected flow rates. If a deficiency in ingredient flow (low or lack of flow) is detected, or higher than expected flow rates are detected, the controller may take actions to compensate for such. The controller 11a may increase or decrease connector connection time so compensate for the deviation in flow rate so as to maintain the amount of ingredient being transferred within specification. Controller 11a may also, for example, change the operating speed of the pump 1010.

On the other hand, if the process cannot be modified by the controller 11a to maintain the product specifications, the controller may generate an error signal to an operator or auditor, or stop the formulation process. In the instance where the auditor is a regulatory entity, such as the FDA, the entity can take immediate action, e.g., prohibit the sale of the product or initiate a recall, rather than do so retrospectively after the product has been distributed or used.

As may be recognized by those of ordinary skill in the pertinent art based on the teachings herein, numerous changes, modifications and improvements may be made to the above-described and other embodiments of the present invention without departing from the scope of the invention as defined in the appended claims. It should be understood that the features disclosed herein can be used in any combination or configuration, and is not limited to the particular combinations or configurations expressly specified or illustrated herein. Thus, in some embodiments, one or more of the features disclosed herein may be used without one or more other feature disclosed herein. In some embodiments, each of the features disclosed herein may be used without any one or more of the other features disclosed herein. In some embodiments, one or more of the features disclosed herein may be used in combination with one or more feature that is disclosed (herein) independently of said one or more features. In some embodiments, each of the features disclosed (herein) may be used in combination with any one or more feature that is disclosed herein independently of said one or more features.

In addition, the invention may be used in conjunction with the disclosures of the following U.S. patent applications, filed on even date herewith, each of which is incorporated herein by reference: entitled "Apparatuses and Methods for Formulating Using a Swirl Chamber" (Ser. No. 15/410,513), which claims priority to similarly-titled U.S. Provisional Patent Application No. 62/280,691, filed Jan. 19, 2016; entitled "Single Use Connectors" (Ser. No. 15/410,762), which claims priority to similarly-titled U.S. Provisional Patent Application No. 62/280,693, filed Jan. 19, 2016; entitled "Pouch with Fitment and Method of Making Same" (Ser. No. 15/410,740), which claims priority to U.S. Provisional Patent Application No. 62/295,139, filed 14 Feb. 2016, U.S. provisional patent application Ser. No. 62/298, 214, filed 22 Feb. 2016, and U.S. provisional patent application Ser. No. 62/323,561, filed 15 Apr. 2016, each of which is entitled "Pouch With Over-Molded Fitment And Method Of Making Same," and U.S. Provisional Patent Application No. 62/280,700, filed 19 Jan. 2016, entitled "Pouch with Heat-Sealed External Fitment." Accordingly, this detailed description of currently preferred embodiments is to be taken in an illustrative, as opposed to a limiting sense.

What is claimed is:

1. An apparatus for controlling transfer of a substance to achieve a predetermined formulation, the apparatus comprising:
    a first connector including unique identification information therefor and in or placeable in fluid connection with a substance to be transferred,
    a second connector configured to cooperate with the first connector to form a substance path between the first connector and the second connector and a fluid-tight seal between the substance path and ambient atmosphere,
    a receiving chamber including unique identification information therefor and in or placeable in fluid connection with the second connector to receive the transferred substance,
    a controller configured to measure one or more of a time or volume of a transfer of the substance near or at an identified component,
    an identifier reader or sensor in or placeable in communication with the controller and configured to read or determine one or more of the unique identification information of the first connector or the unique identification information of the receiving chamber,
    a connecting device in or placeable in communication with the controller and configured to connect and disconnect substance flow one or more of to or from one or more of the first or second connectors,
    wherein the controller is configured to compare the measured one or more of said time or said volume to a respective predetermined time or respective predetermined volume, and to adjust one or more of the time or the volume of the transfer.

2. The apparatus of claim 1, wherein the controller is configured to control transfer of two or more substances into the receiving chamber.

3. The apparatus of claim 1, wherein the controller is configured to adjust one or more of a time or a volume of a substance to obtain a predetermined formulation.

4. The apparatus of claim 1, wherein the identifier reader or sensor is configured to record one or more of the unique identification information of the first connector or the unique identification information of the receiving chamber.

5. The apparatus of claim 1, further comprising a source of the substance being transferred including unique identification information therefor in or placeable in fluid connection with the first connector.

6. The apparatus of claim 1, wherein the fluid-tight seal comprises a hermetic seal.

7. The apparatus of claim 4, wherein the identifier reader or sensor is configured for automatic reading of the one or more of the unique identification information of the first connector or the unique identification information of the receiving chamber during one or more of: prior to, during, or after completion of a transfer of substance.

8. The apparatus of claim 1, further comprising a flow meter configured to measure a flow rate of the substance at or near a point of connection of the first and second connectors.

9. The apparatus of claim 8, wherein the flow meter is configured to measure the flow rate without contacting the transferred substance.

10. The apparatus of claim 9, wherein the flow rate is measured using one or more of: optical, laser, ultrasonic, or magnetic techniques.

11. The apparatus of claim 8, wherein the flow meter is configured to communicate an electronic signal to the controller representing the flow rate, and wherein the controller comprises a process logic controller (PLC).

12. The apparatus of claim 1, configured to aseptically transfer the substance from the first connector to the receiving chamber in an ambient environment that is one or more of not sterile or not particle-free.

13. The apparatus of claim 1, wherein the connecting device is in communication with the controller, which comprises a process logic controller (PLC), and wherein the connecting device is configured to receive a signal from the controller to disconnect substance flow one or more of to or from one or more of the first or second connector.

14. The apparatus of claim 1, the apparatus further comprising:
    a cradle having a body defining a first interior cavity portion therein configured to receive therein a fluid transfer connector formed by the connection of the first connector and the second connector, wherein the cradle is configured and dimensioned to receive the fluid transfer connector therein only when the first connector and the second connector are properly connected together.

15. The apparatus of claim 14, wherein the first interior cavity portion includes at least a portion of the identifier reader or sensor configured to read or determine the unique identification information of the first connector, and the apparatus is further configured to transmit said unique identification information of the first connector to the controller, which is configured to control fluid transfer flow though the fluid transfer connector.

16. The apparatus of claim 15, wherein the unique identification information of the first connector is contained in an RFID tag included on or in the first connector, and the identifier reader or sensor includes an RFID reader.

17. The apparatus of claim 15, wherein the unique identification information of the first connector is contained in a barcode contained on the first connector, and the identifier reader or sensor includes a bar code reader.

18. The apparatus of claim 14, further including a detector configured to detect whether the fluid transfer connector is properly located within the first interior cavity portion, and to transmit to the controller, which is configured to control fluid transfer flow though the fluid transfer connector, information representing that the fluid transfer connector is properly located within the first interior cavity portion.

19. The apparatus of claim 18, wherein the detector is mechanical, electromechanical, or electronic.

20. The apparatus of claim 18, wherein the detector includes a switch having and movable between a first position when the connector is not properly located in the first interior cavity portion and a second position when the connector is properly located in the first interior cavity portion, and configured to, in the second position, transmit information to the controller representing that the fluid transfer connector is properly located within the first interior cavity portion.

21. The apparatus of claim 20, wherein the switch is biased in a direction from the second position toward the first position.

22. The apparatus of claim 14, wherein the cradle further defines a second interior cavity portion configured to receive therein a portion of a flow conduit in or placeable in fluid communication with the fluid transfer connector, and includes a flow meter configured to measure flow of fluid through the flow conduit, wherein the apparatus is further configured to transmit said flow measurement to the controller, which is configured to control fluid transfer flow though the fluid transfer connector.

23. The apparatus of claim 14, further comprising a cover movable relative to the body between an open position and a closed position, wherein in the closed position the cover sufficiently blocks access to the first interior cavity portion to prevent (1) insertion of said fluid transfer connector into the first interior cavity portion when the fluid transfer connector is not located in the cradle and 2) removal of said fluid transfer connector from the first interior cavity when the fluid transfer connector is located within the cradle, and an open position where the cover does not block access the first interior cavity portion to allow (1) insertion of said fluid transfer connector into the first interior cavity portion when the fluid transfer connector is not located in the cradle and 2) removal of said fluid transfer connector from the first interior cavity when the fluid transfer connector is located within the cradle.

24. The apparatus of claim 23, further including a cover position detector configured to detect whether the cover is in an open position or a closed position, and to transmit to the controller, which is configured to control fluid transfer flow though the fluid transfer connector, information representing that the cover is in the closed position.

25. The apparatus of claim 24, wherein the cover position detector is mechanical, electromechanical, or electronic.

26. The apparatus of claim 24, wherein the cover position detector includes a switch having and movable between a first position when the cover is in the open position and a second position when the cover is in the closed position, and configured to, in the second position, transmit information to the controller representing that the cover is in the closed position.

27. The apparatus of claim 26, wherein the switch is biased in a direction from the second position toward the first position.

28. The apparatus of claim 23, wherein the body defines at least one opening therein configured to permit viewing of the fluid transfer connector in the cradle when the cover is in the closed position.

29. A method comprising:
controlling transfer of a substance to achieve a predetermined formulation using an apparatus including a first connector including unique identification information therefor and in or placeable in fluid connection with a substance to be transferred, a second connector configured to cooperate with the first connector to form a substance path between the first connector and the second connector and a fluid-tight seal between the substance path and ambient atmosphere, a receiving chamber including unique identification information therefor and in or placeable in fluid connection with the second connector to receive the transferred substance, an identifier reader or sensor in or placeable in communication with a controller, and a connecting device in or placeable in communication with the controller and configured to connect and disconnect substance flow one or more of to or from one or more of the first or second connectors, the method comprising:
measuring with the controller one or more of a time or a volume of the transfer of the substance near or at an identified component;
comparing with the controller one or more of the measured time to a respective predetermined time or the measured volume to a respective predetermined volume, and
adjusting with the controller one or more of the time or the volume of the transfer.

30. The method of claim 29, further comprising adjusting a transfer of two or more substances into the receiving chamber.

31. The method of claim 29, further comprising obtaining a predetermined formulation by performing the adjusting step.

32. The method of claim 29, further comprising recording with the identifier reader or sensor one or more of the unique identification information of the first connector or the unique identification information of the receiving chamber.

33. The method of claim 29, further comprising forming a fluid connection between (i) a source of the substance being transfered including unique identification information therefor and (ii) the first connector, and transferring substance therebetween.

34. The method of claim 29, wherein the fluid-tight seal comprises a hermetic seal.

35. The method of claim 32, further comprising, with the identifier reader or sensor, automatically reading the one or more of the unique identification information of the first connector or the unique identification information of the receiving chamber during one or more of: prior to, during, or after completion of a transfer of substance.

36. The method of claim 29, further comprising measuring with a flow meter a flow rate of the substance at or near a point of connection between the first and second connectors.

37. The method of claim 36, wherein the step of measuring the flow rate is performed without contacting the transferred substance.

38. The method of claim 37, wherein the step of measuring the flow rate includes measuring the flow rate using one or more of: optical, laser, ultrasonic, or magnetic techniques.

39. The method of claim 36, further comprising the flow meter communicating an electronic signal to the controller representing said flow rate, wherein the controller comprises a process logic controller (PLC).

40. The method of claim 29, including aseptically transferring the substance in an ambient environment that is one or more of not sterile or not particle-free.

41. The method of claim 29, wherein the controller comprises a PLC, and further comprising the connecting device communicating with the controller to receive a signal from the PLC to disconnect substance flow one or more of to or from one or more of the first or second connector.

42. The method of claim 29, further comprising:
placing a fluid transfer connector including the first connector and the second connector into a properly connected position by connecting the first and second connectors; and
inserting the properly connected fluid transfer connector into a cradle having a body defining a first interior cavity portion therein configured to receive therein said fluid transfer connector only when the first connector and the second connector are properly connected together, such that the fluid transfer connector is received in the first interior cavity portion.

43. The method of claim 42, further including sensing the unique identification information of the first connector, and transmitting said unique identification information of the first connector to the controller, which is configured to control fluid transfer flow though the connector.

44. The method of claim 43, wherein the unique identification information of the first connector is contained in an RFID tag, and the sensing step includes sensing said unique identification information of the first connector with an RFID reader.

45. The method of claim 43, wherein the unique identification information of the first connector is contained in a barcode contained on the first connector, and the sensing step includes sensing said unique identification information of the first connector with a barcode reader.

46. The method of claim 42, further including detecting whether the fluid transfer connector is properly located within the first interior cavity portion, and transmitting to the controller, which is configured to control fluid transfer flow though the fluid transfer connector, information representing that the fluid transfer connector is properly located within the first interior cavity portion.

47. The method of claim 46, further including transferring fluid through said fluid transfer connector only when said fluid transfer connector is properly located within the first cavity portion.

48. The method of claim 46, wherein the detecting step includes moving a switch from a first position where the fluid transfer connector is not properly located in the first interior cavity portion to a second position where the fluid transfer connector is properly located in the first interior cavity portion, and then transmitting said information to the controller representing that the fluid transfer connector is properly located within the first interior cavity portion.

49. The method of claim 48, further including biasing the switch in a direction from the second position toward the first position.

50. The method of claim 42, wherein the cradle further defines a second interior cavity portion configured to receive therein a portion of a flow conduit in or placeable in fluid communication with the fluid transfer connector, and includes a flow meter configured to measure flow of fluid through the flow conduit, and the method further includes inserting said flow conduit portion in the second interior cavity portion and transmitting a measurement of fluid flow through said flow conduit portion to the controller, which is configured to control fluid transfer flow though the fluid transfer connector.

51. The method of claim 42, wherein the cradle includes a cover movable relative to the body between an open position and a closed position, and the method further includes moving the cover from the open to the closed position and transmitting to the controller, which is configured to control fluid transfer flow though the fluid transfer connector, information representing that the cover is in the closed position.

52. The method of claim 51, further including detecting whether the cover is in the open position or the closing position prior to the transmitting step.

53. The method of claim 52, wherein the detecting step includes moving a switch from a first position where the cover is in the open position to a second position where the cover is in a closed position.

54. The method of claim 53, further including biasing the switch in a direction from the second position toward the first position.

55. The method of claim 42, further including engaging a flow conduit in or placeable in fluid communication with the fluid transfer connector with a pump configured to pump fluid in the flow conduit through the connector in the properly connected position.

* * * * *